US005627025A

United States Patent [19]
Steinman et al.

[11] Patent Number: 5,627,025
[45] Date of Patent: May 6, 1997

[54] METHOD FOR THE IDENTIFICATION OF COMPOUNDS CAPABLE OF ABROGATING HUMAN IMMUNODEFICIENCY VIRUS (HIV) INFECTION OF DENDRITIC CELLS AND T-LYMPHOCYTES

[75] Inventors: Ralph M. Steinman, Westport, Conn.; Melissa Pope, New York, N.Y.; Michiel Betjes, Amsterdam, Netherlands; Lloyd Hoffman, Great Neck, N.Y.

[73] Assignee: The Rockefeller University, New York, N.Y.

[21] Appl. No.: 290,432

[22] Filed: Aug. 12, 1994

[51] Int. Cl.⁶ .................... C12Q 1/70; G01N 33/53; G01N 33/567; G01N 33/555

[52] U.S. Cl. .................... 435/5; 435/7.2; 435/7.24; 436/63

[58] Field of Search ............... 435/5, 7.2, 7.24; 424/208.1; 436/63

[56] References Cited

PUBLICATIONS

Cameron et al., 1994, AIDS Res. Hum. Retroviruses 10: 61–71.
Cimarelli et al., 1994, J. Acquir. Immune. Defic. Syndr. 7:230–235.
Nestle et al., 1994, Cell. Immunol. 156:220–229.
Taylor, 1994, J. NIH Res. 6:26–7.
Bhardwaj et al., 1993, J. Exp. Med. 178: 633–642.
Embretson et al., 1993, Nature 362:359–362.
Liu and MacPherson, 1993, J. Exp. Med. 177:1299–1307.
O'Doherty et al., 1993, J. Exp. Med. 178:1067–1078.
Pantaleo et al., 1993, Nature 362:355–358.
Berger et al., 1992, J. Invest. Dermatol. 99:271–277.
Cameron et al., 1992, Science 257: 383–387.
Miller et al., 1992, Lab. Invest. 68:129–145.
Miller et al., 1992, Lab. Invest. 67:628–634.
Sornasse et al., 1992, J. Exp. Med. 175:15–21.
Kalter et al., 1991, J. Immunol. 146, 3396–3404.
Larsen et al., 1990, J. Exp. Med. 172:1483–1493.
Mackay et al., 1990, J. Exp. Med. 171:801–818.
Zack et al., 1990, Cell 61:213–222.
Bujdoso et al., 1989, J. Exp. Med. 170:1285–1302.
Rhodes et al., 1989, Immunol. 68:403–409.
Austyn et al., 1988, J. Exp. Med. 167–646–651.
Kaplan et al., 1987, J. Exp. Med. 165, 763–776.
Giannetti et al., 1993, "Direct detection of HIV–1 RNA in epidermal Langerhans cells of HIV–infected patients", J. Acquir. Immune Defic. Syndr. 6:329–333.

*Primary Examiner*—Christine M. Nucker
*Assistant Examiner*—Jeffrey S. Parkin, Ph.D.
*Attorney, Agent, or Firm*—Klauber & Jackson

[57] ABSTRACT

The present invention relates to the role of dendritic cells in facilitating productive human immunodeficiency virus (HIV) infection. Experimentally, productive infection with HIV-1 requires that virus be administered to T cells that are activated by mitogens. This application describes a productive milieu for HIV-1 infection within the confines of normal epithelial tissue that does not require standard stimuli. The milieu consists of dendritic cells and T cells that emigrate from skin and produce distinctive stable, nonproliferating conjugates. These conjugates, upon exposure to HIV-1, begin to release high levels of virus progeny. Numerous infected syncytia, comprised of both dendritic cells and T cells, rapidly develop. A method is disclosed for the identification of agents capable of inhibiting HIV transmission and chronic infection of dendritic cells and T lymphocytes found in epithelial tissues.

12 Claims, 13 Drawing Sheets

FIG.2A
FIG.2B
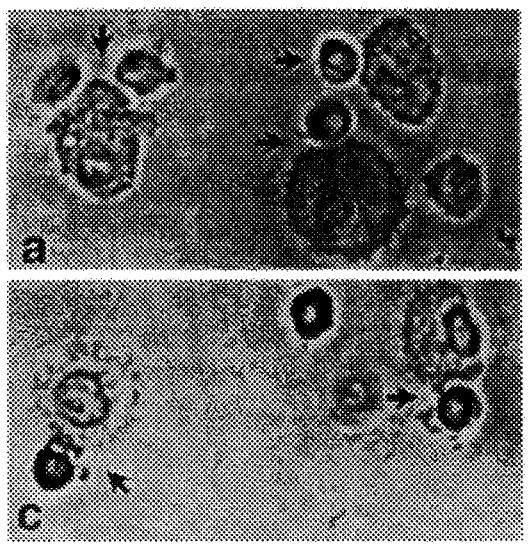
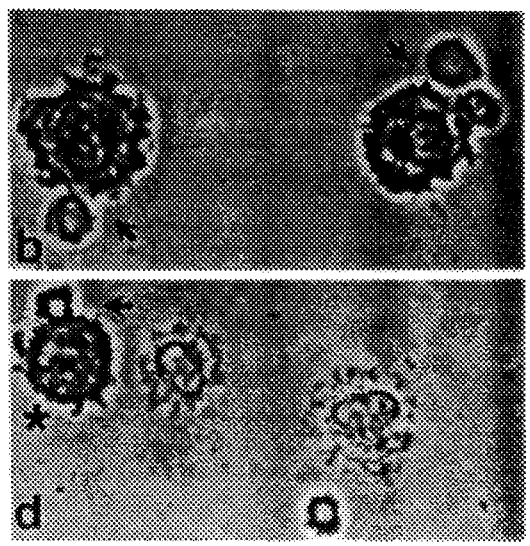
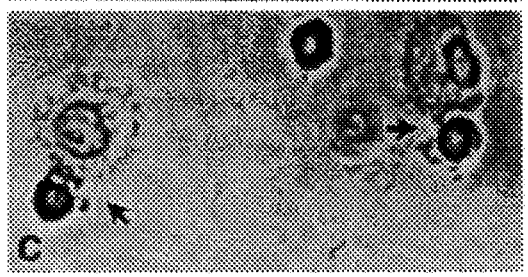
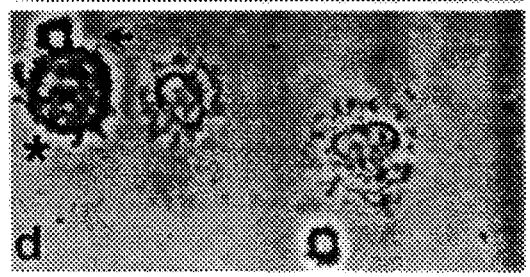
FIG.2C
FIG.2D

Strategy I

Strategy II

Strategy II

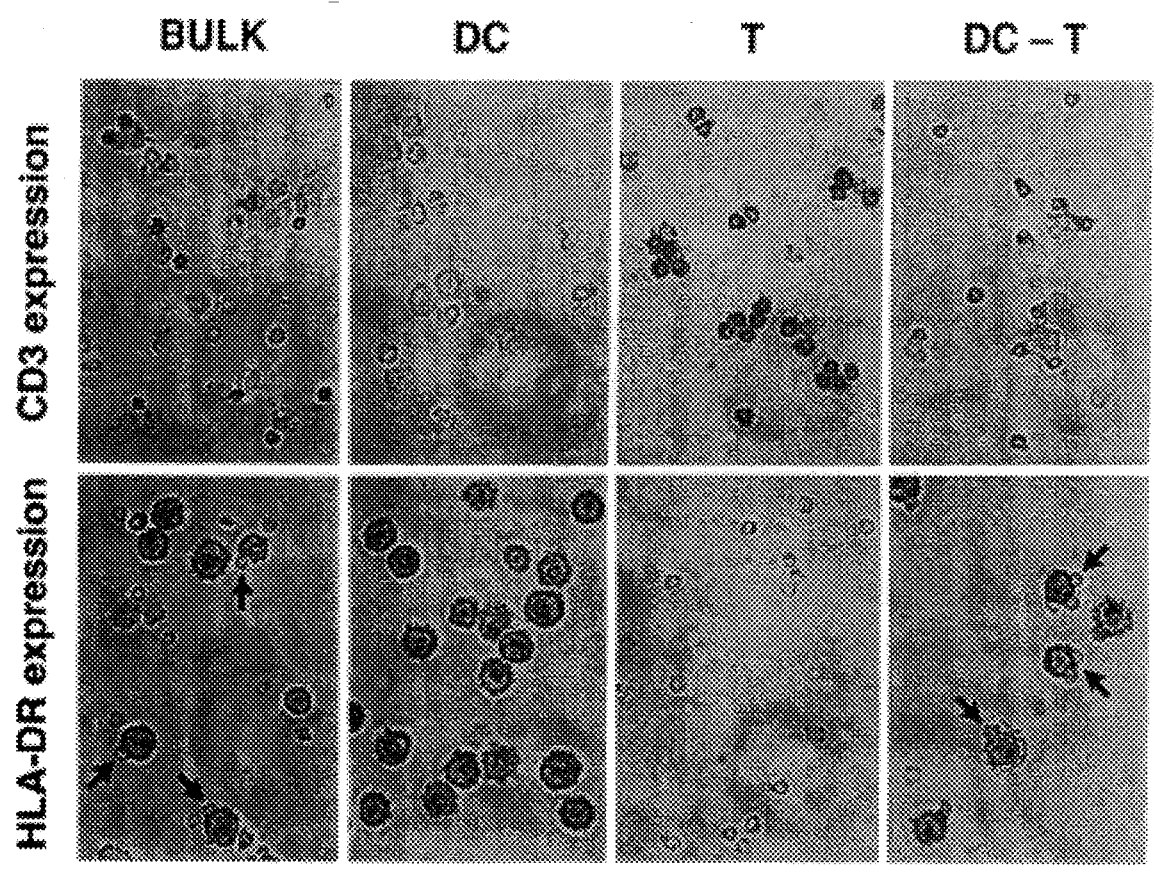

FIG. 7A
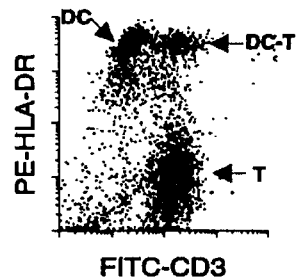
FIG. 7B
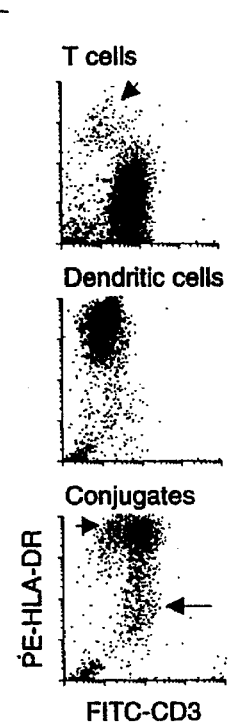
FIG. 7C
Characterization of profiles in sorted dendritic-T cell conjugates
|  | CD3+ | CD3- | HLA-DR+ | HLA-DR- |
|---|---|---|---|---|
| Small cells | | | | |
| Expt 1 | 375 | 4 | 4 | 360 |
| Expt 2 | 437 | 6 | 4 | 495 |
| Expt 3 | 310 | 1 | 0 | 308 |
| Large cells | | | | |
| Expt 1 | 0 | 321 | 378 | 4 |
| Expt 2 | 0 | 363 | 429 | 3 |
| Expt 3 | 0 | 313 | 352 | 2 |
FIG. 7D
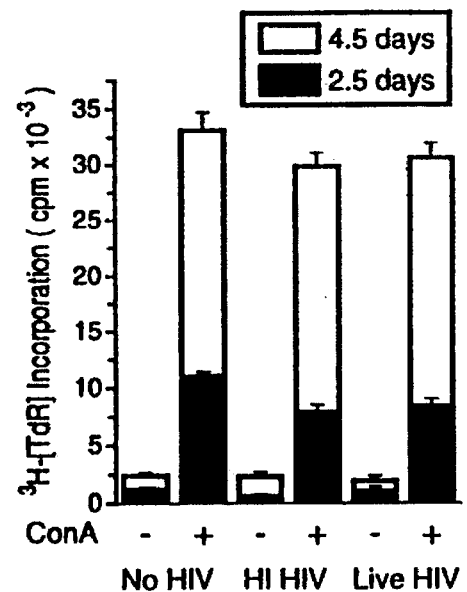

FIG.11A
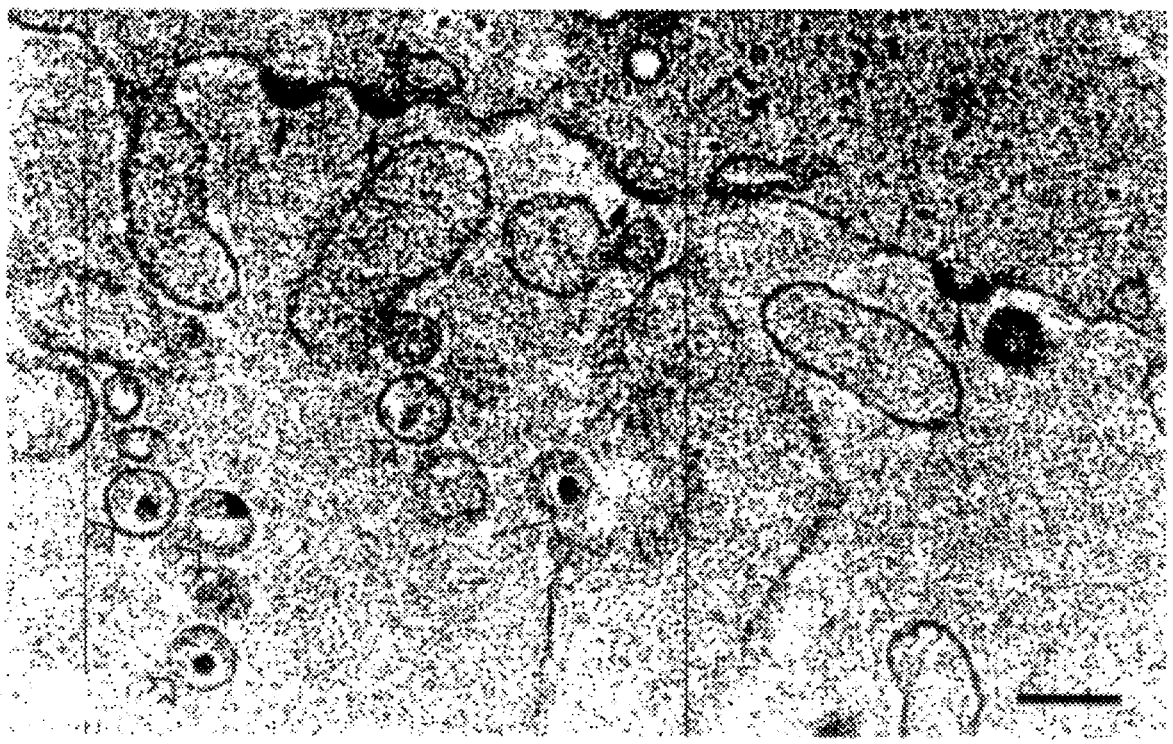
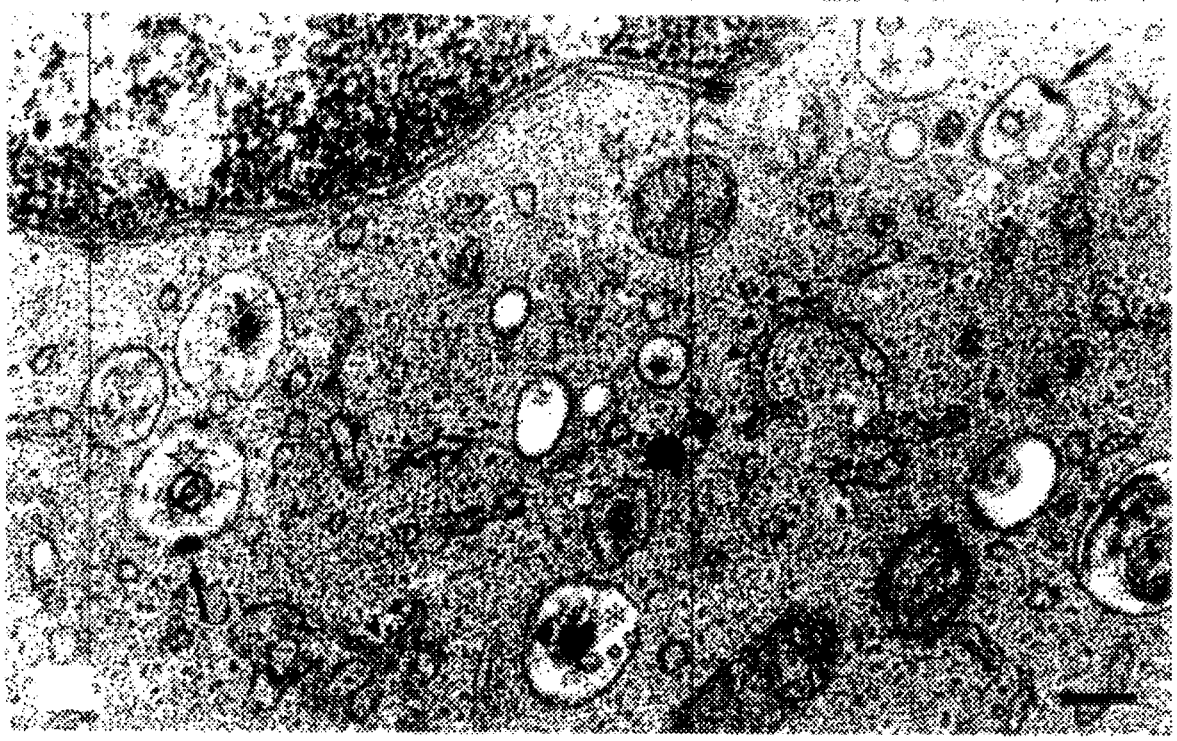
FIG.11B

METHOD FOR THE IDENTIFICATION OF COMPOUNDS CAPABLE OF ABROGATING HUMAN IMMUNODEFICIENCY VIRUS (HIV) INFECTION OF DENDRITIC CELLS AND T-LYMPHOCYTES

The research leading to the present invention was supported in part with Grant Nos. AI24775 and AI07012 from the National Institutes of Health. The Government may have certain rights in the invention.

FIELD OF THE INVENTION

The present invention relates to the role of dendritic cells in immune responses, and the transmission and infectivity of the human immunodeficiency virus. The invention further relates to identification of agents capable of modulating the immunological functional activity of dendritic cells, and agents capable of inhibiting the transmission or infectivity, or both, of HIV.

BACKGROUND OF THE INVENTION

Dendritic Cell Migration and Maturation

Amongst the distinctive features of dendritic cells are their migratory properties. Migration has been studied to a large extent in skin. During contact sensitivity, dendritic cells (Langerhans cells) are noted in the afferent lymph (Lens et al., 1983; Silberberg-Sinakin et al., 1976) and in the draining lymph node (Kripke et al., 1990; Macatonia et al., 1987). Following skin transplantation, dendritic cells leave the epidermis and undergo changes that include increased expression of MHC class II (Larsen et al., 1990). Since dendritic cells are known to gain access to afferent lymphatics (Knight et al., 1982; Lens et al., 1983; Pugh et al., 1983; Rhodes et al., 1989), the migration of these potent antigen presenting cells into the lymph and then to the draining lymph node, may account for the need for intact, cutaneous afferent lymphatics during the primary response to transplants (Barker and Billingham, 1968) and contact allergens (Frey & Wenk, 1957) in situ. In recall or delayed type hypersensitivity reactions, dendritic cells also are juxtaposed to the infiltrates of dermal mononuclear cells (Kaplan et al., 1987).

When dendritic cells are pulsed with antigens ex vivo and are injected into mice, $CD4^+$ T cells are primed in the draining lymphoid organs (Inaba et al., 1990; Liu and MacPherson, 1993; Sornasse et al., 1992). Austyn et al. showed that dendritic cells, when placed into the blood stream or paws of mice, migrate to the T cell areas in the draining lymphoid tissue, i.e., spleen and lymph node respectively (Austyn et al., 1988). If antigens are deposited intramuscularly, the dendritic cells from the corresponding afferent lymphatics carry that antigen in a form stimulatory for T cells (Bujdoso et al., 1989). Therefore, the migratory properties of dendritic cells likely interface with their antigen presenting functions to sensitize T cells in situ.

Human Immunodeficiency Virus Infection

An early and likely critical deficit during infection with HIV-1 is a loss of immunologic memory in the $CD4^+$ T helper compartment (Murray et al., 1985; Lane et al., 1985; van Noesel et al., 1994). There is a loss of reactivity to test antigens in vivo (delayed type hypersensitivity responses) and a loss of T cell function in culture. It is clear that HIV-1 can infect and kill $CD4^+$ T cells that are responding to antigens and superantigens (Cameron et al., 1994).

However, in what sites of an infected individual is HIV-1 being generated, and why is reduced $CD4^+$ T cell memory such an early and profound occurrence?

The presence of virus in individuals infected with HIV-1 is clearly documented. In blood, infectious virus (Ho et al., 1989; Coorobs et al., 1989), numerous viral particles (Piatak Jr. et al., 1993), and cells with HIV-1 transcripts (Saksela et al., 1994) are present. These manifestations of a significant virus burden appear to increase progressively during disease. In lymphoid tissues, particularly in the germinal center regions, even larger burdens of HIV-1 can be identified relative to blood (Armstrong and Horne, 1984; Biberfeld et al., 1986; Racz et al., 1986; Spiegel et al., 1992; Pantaleo et al., 1993; Embretson et al., 1993). Lymphoid germinal centers contain "germinating" or proliferating B cells that undergo clonal selection most likely via immune complexes that are retained on the surface of follicular dendritic cells (reviewed by (Gray, 1993) and (Szakal et al., 1989)]. The burden of HIV-1 in lymphoid organs appears to be associated with these follicular dendritic cells (Armstrong and Horne, 1984; Pantaleo et al., 1993). Given the capacity of follicular cells to retain immune complexes (Hanna and Szakal, 1968; Nossal et al., 1968; Chen et al., 1978; Humphrey et al., 1984), and the presence of virions and antibody in plasma, much of the virus in germinal centers may represent immune complexes of virions that are produced elsewhere.

Another class of dendritic cell that differs from the follicular dendritic cell may be important for the production, as opposed to the accumulation, of HIV-1 virions in situ. These dendritic cells are a) bone marrow-derived, b) localized to the T cell area of lymphoid organs, and c) specialized in many ways to present processed antigens to both $CD4^+$ and $CD8^+$ T cells (reviewed in (Steinman, 1991)). Such features stand in contrast to follicular dendritic cells which a) do not appear to be bone marrow-derived and b) function in the germinal centers to c) present intact (not processed) antigens to B cells. Bone marrow-derived dendritic cells are of interest because experimentally, the major site for productive infection with HIV-1 is the stimulated $CD4^+$ T cell (Klatzmann et al., 1984; Zack et al., 1990). Antigen presenting dendritic cells are specialized to create a stable (days) microenvironment rich in responding $CD4^+$ T cells (Inaba and Steinman, 1984; Inaba and Steinman, 1986; Pancholi et al., 1992; Bhardwaj et al., 1994). When human blood dendritic cells are pulsed with HIV-1 and then present antigen or super antigen in this microenvironment, the dendritic cells are not infected, but virus is efficiently transferred to the responding T cells (Cameron et al., 1992; Cameron et al., 1994).

According to the World Health Organization, more than 75% of new HIV infections occur during heterosexual sex; many more result from male homosexual relations. Sexual contact involves the mucous membranes in the vagina, penis, rectum, and oral cavity. To date, apart from physical barriers such as condoms, there is no effective way to prevent the spread of HIV infection, and AIDS. In particular, there is no vaccine for HIV, and the prospect of developing an HIV vaccine within the next few years are dim. Since individuals reluctantly change sexual practices, including condom use, the prospects for controlling transmission through behavior are not much better. An attractive third strategy for preventing HIV infection that has lately garnered considerable attention is application of a topical microbicide to the affected areas, e.g., skin and mucous membranes (see, e.g., Taylor, 1994, J. NIH Res. 6: 26–27). Finding compounds that can block HIV-1 transmission during sex is becoming a high priority for public health officials in the U.S. and abroad (ibid.). Thus, there is a clear need in the art for an assay to identify such compounds. Such an assay relies on understanding the mechanism of sexual transmission of HIV.

The citation of any reference herein should not be construed as an admission that such reference is prior art to the instant invention. Full citations for references cited by author and year are found at the end of the specification.

SUMMARY OF THE INVENTION

The present invention provides a method for identifying an agent capable of modulating dendritic cell function. Dendritic cell functions include migration from skin and related tissues (e.g., that contain stratified squamous epithelium, such as, but not limited to, mucous membranes), interaction with cutaneous T cells, and maturation. In broad aspect, the method comprises the in vitro steps of: exposing or contacting a first skin explant with an agent to be assayed for its ability to modulate dendritic cell function; floating the first skin explant dermal side down in culture medium at 37° C.; floating a second skin explant, which is not exposed or contacted with the agent, dermal side down in culture medium at 37° C.; and determining whether dendritic cells that have migrated from the first skin explant and are present in the culture medium and dendritic cells that have migrated from the second skin explant and are present in the culture medium demonstrate differences in a functional activity. According to the invention, a difference in the number, ability to associate with cutaneous T cells, or activity of dendritic cells from the first explant in the culture medium compared to the number, ability to associate with cutaneous T cells, or activity of dendritic cells from the second explant indicates that the agent is capable of modulating dendritic cell function. In a specific aspect, evaluation of dendritic cell functional activity comprises evaluating a difference in the number of dendritic cell-T lymphocyte conjugates from the first explant in the culture medium compared to the number of dendritic cell-T lymphocyte explants from the second explant in the culture medium lacking the agent to determine whether an agent is capable of modulating dendritic cell function. Other criteria for evaluating dendritic cell functional activity include the capacity to stimulate allogeneic T cell proliferation, and the ability to process antigen.

The invention relies on the understanding that dendritic cell functional activity includes migration from skin or mucous membrane tissue and maturation. Maturation can be reflected by properties such as, but not limited to, conjugation with peripheral T lymphocytes present in the skin or mucous membrane tissue prior to or coincidently with migration, processing and presentation of antigen, and activation of resting T lymphocytes. The instant invention advantageously characterizes the ability of dendritic cells to interact with autologous resting T lymphocytes in the skin.

The invention is particularly useful to identify agents that inhibit dendritic cell migration or maturation, or both, which may be applied to the skin to prevent or alleviate contact allergies. For example, an agent that tolerates migration but inhibits maturation is useful for treating contact allergy, in which presentation of contact allergen by immature dendritic cells may tolerize the host to the allergen. An agent that prevents the association of dendritic cells with cutaneous T lymphocytes could block an immune response. Alternatively, agents identified according to the invention that promote dendritic cell migration and maturation can be important adjuvants in conjunction with a transdermal or intradermal vaccine. The invention advantageously provides a simple in vitro model for this important in vivo activity of dendritic cells. This model is a powerful tool for drug discovery and evaluation.

In a further aspect, the invention relates to a method for identifying an agent capable of inhibiting HIV transmission and chronic infection via dendritic cells and T lymphocytes found in skin, and related tissues, e.g., that contain stratified squamous epithelium, such as, but not limited to, mucous membranes. This method comprises the in vitro steps of: exposing or contacting a first skin explant with an agent to be assayed for its ability to inhibit HIV infection of dendritic cells; floating the first skin explant dermal side down in culture medium at 37° C.; floating a second skin explant, which has not been exposed to or contacted with the agent, dermal side down in culture medium at 37° C.; contacting both the first and the second skin explants with an HIV isolate; and determining whether cells in the culture medium that have migrated from the first skin explant are infected with HIV, and whether cells in the culture medium that have migrated from the second skin explant are infected with HIV. According to the invention, a decrease in the level of HIV infection in the cells from the first explant in the culture medium compared to the level of HIV infection in the cells from the second explant indicates that the agent is capable of inhibiting HIV infection of dendritic cells and T lymphocytes. A specific Example discloses that productive HIV infection occurs in dendritic cell-T cell conjugates, but not in either cell type alone.

The behavior of dendritic cells and T cells that migrate from skin explants in vitro is believed to be analogous to the activity of these cell types in skin and layered squamous epithelial tissue in vivo. The primary routes of transmission of HIV are through the anal, vaginal, cervical, and oral epithelium. Thus, an further important advantage of the invention that it provides a powerful in vitro assay to screen for drugs that can inhibit HIV transmission and infectivity. Such drugs may be identified using the more general dendritic cell functional activity modulation assay. Of particular relevance is identification of an agent that can inhibit interaction of dendritic cells with cutaneous or memory T cells. Since infectivity of HIV is closely associated with formation of such complexes, an agent capable of blocking such conjugate formation may be a potent drug in the arsenal against HIV infection, transmission, and chronic T cell depletion involved with AIDS.

Memory T cells contact dendritic cells, including HIV infected dendritic cells, present in skin or mucous membranes. Contact of memory T cells with infected dendritic cells, which may act as a reservoir for HIV infectivity, fosters chronic HIV infection. Contact of memory T cells with HIV infected dendritic cells may also provide a mechanism for the infection of these important immune cells, and explains the persistent elimination of CD4-positive T lymphocytes characteristic of HIV infection. Reduction in the number of T lymphocytes is probably the single most important factor leading to the onset of AIDS.

Thus, is it a primary object of the invention to provide an in vitro assay to identify agents that modulate dendritic cell functional activity.

In particular, it is an object of the invention to provide an in vitro assay system to identify agents that inhibit dendritic cell migration, or dendritic cell maturation, or both.

It is a further particular object of the invention to provide an in vitro assay system to identify agents that promote dendritic cell migration, or dendritic cell maturation, or both.

Accordingly, an object of the invention is to identify an agent that modulates dendritic cell functional activity, e.g., and agent that inhibits or promotes dendritic cell migration or maturation, or both; preferably, the agent modulates the interaction of dendritic cells with cutaneous T cells.

An important object of the invention is to provide an in vitro assay system to identify agents that can inhibit chronic or acute HIV infection of dendritic cells and peripheral (cutaneous) T lymphocytes.

A further related object of the invention is to identify an agent that can prevent or inhibit transmission of HIV, e.g., by sexual contact.

An additional related object of the invention is to identify an agent that can prevent chronic infection and destruction of T lymphocytes, particularly memory T lymphocytes, fostered by HIV infected dendritic cells.

These and other objects of the invention will be better understood by reference to the accompanying Figures and Detailed Description of the Invention.

DESCRIPTION OF THE DRAWINGS

FIG. 2 Features of emigrated skin cells in cytospin preparations. Skin emigrés were immunoperoxidase stained with anti-HLA-DR (a), anti-CD3 (b), or anti-CD4 (c). Conjugates are indicated with arrows. Dendritic cells are strongly HLA-DR$^+$, but the lymphocytes are DR$^-$ (a). Contrariwise, the lymphocytes are CD3$^+$, and the dendritic cells CD3$^-$ (b). CD4$^+$ lymphocytes, free and bound, are present (c). Although Langerhans cells express CD4 (Wood et al., 1983), less than 10% of emigrated dendritic cells were stained by the immunoperoxidase method (*, this cell stained with a blush of color on the original cytosp, in). Representative fields from 1 of 6 identical experiments are shown. Scale bar, 10 μm.

FIG. 5 efficiency of separation of skin emigrés by cell sorting. Cytospins were prepared of bulk skin cells (BULK) (A, E), and the three sorted cell populations: dendritic cells, DC (B, F); T cells, T (C, G); and dendritic cell-T cell conjugates, DC-T (D, H). Each cytospin was immunoperoxidase stained with either anti-CD3 (top row, A–D) or anti-HLA-DR (bottom row, E–H). Dendritic cell-T cell conjugates are highlighted with arrows. These observations have been made on 10 separate occasions. Scale bar, 20 μm.

FIG. 7 Emigration of nonproliferating dendritic cells, T cells, and dendritic cell-T cell conjugates from human skin explants. A. FACScan analysis of the emigrés from skin organ cultures after double-labeling with monoclonals to T cells (anti-CD3) and dendritic cells (anti-HLA-DR). Three populations routinely were present (arrows): HLA-DR$^+$, CD3$^-$ dendritic cells (DC); HLA-DR$^-$, CD3$^+$ T cells (T); and dendritic cell-T cell conjugates (DC-T). Staining results with the PE-isotype control fell in the first decile of the log scale. The lower HLA-DR stain on a minor fraction of dendritic cells and conjugates, probably reflects an origin from the dermis rather than the epidermis. B. Reanalysis of the 3 cell populations in FIG. 1A following cell sorting and staining with anti-HLA-DR and anti-CD3 monoclonals. A 2% contamination of the free T cells with dendritic cells is evident (top panel, arrow). About 10% of the conjugated fraction disassemble in to free dendritic cells (arrowhead) and small T cells (arrow) (Methods and FIG. 1C). C. Characterization of the sorted dendritic-T cell conjugate fraction by immunoperoxidase labeling with anti-CD3 and anti-HLA-DR. Small cells are 10 μm in diameter and large cells, >25 μm diameter. D. DNA synthesis in skin emigres ($4 \times 10^4$ cells/well in a 96 well round-bottomed tray) that were cultured in the absence or presence of HIV-1, either live virus or heat-inactivated (HI) HIV. In some cultures, the mitogen ConA was added (+) at 3 μg/ml (after pulsing cells with virus) as a positive control for T cell proliferative potential, as monitored by $^3$H-(TdR) uptake on the 3rd and 5th day (filled and open bars, respectively). Blood mononuclear cells incorporated in the range of 250–1000 cpm of $^3$H-(TdR) (not shown).

FIG. 11 Electron microscopic evidence for production of HIV-1 virions in syncytia. EM was performed on skin cells, 4 days after exposure to HIV-1$_{IIIB}$. High magnification of budding virus (A, arrows) and free virus (A, open arrow) at a magnification of 68,000X. Budding could also be observed intracellularly (B, arrows) at a magnification of 48,000X.

DETAILED DESCRIPTION OF THE INVENTION

Figure 1A:
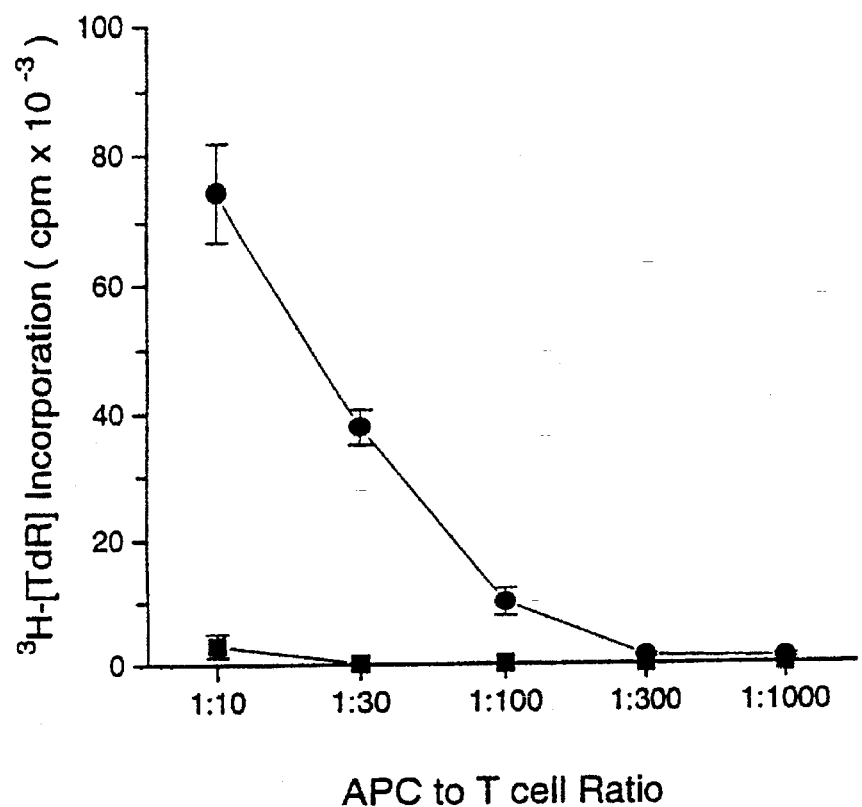
FIG. 1 Strong T cell stimulatory activity of cells emigrating from skin explants. Activity was assessed by adding graded doses of irradiated (1500 rads $^{137}$Cs) skin-derived cells to a constant number ($1.5 \times 10^5$) of allogeneic T cells in flat-bottomed microtest wells. After 5 days, $^3$H-(TdR) at 1 μCi/well was added for 12 hr. Potency is reflected by the activity of the skin cells relative to the standard stimulator population used in tissue typing, i.e., peripheral blood mononuclear cells or PBMC (■). A. The stimulators were derived by emigration from skin explants (●). B. The stimulators were obtained from separated epidermis (▲) or dermis (♦) as described (Macatonia et al., 1987; Silberberg-Sinakin et al., 1976). Error bars represent mean±SEM of triplicate cultures from 1 of 4 similar experiments.

As noted above, the present invention relates to a method for identifying an agent capable of modulating dendritic cell function. The invention particularly relates to identification of an agent that can prevent or inhibit infection of dendritic cells and associated T lymphocytes with the human immunodeficiency virus (HIV). The present invention relates further to compositions comprising such agents that have been so identified. The term "modulation," in all of its grammatical forms, refers to the ability of an agent to increase or decrease (promote or inhibit one or more functional activities of a dendritic cell.

The invention targets assays to the functional activity of dendritic cells present in skin and tissues that are histologically and immunologically similar to skin. Such dendritic cells are usually called Langerhans cells, and differ from the follicular dendritic cells found in lymphatic tissue, as discussed above. Such dendritic cells may be referred to as cutaneous dendritic cells. Furthermore, skin provides an accessible model for the behavior of dendritic cells in related tissues. In particular, the present invention relates to the functional activity of dendritic cells in mucous membranes, which are histologically and immunologically similar to skin. As used herein, the term "mucous membrane" refers to vaginal, cervical, penile, rectal, anal, and oral epithelium and the underlying tissue (the equivalent of the dermis of the skin). Mucous membranes and skin contain stratified squamous epithelium and underlying layers. Most of the T cells and many dendritic cells are found in the underlying layers.

As used herein, the term "functional activity" and the like relates to the changes in the location, phenotype, morphology, cytokine production, and other characteristics and properties of dendritic cells. One functional activity of dendritic cells is the ability to migrate from skin. Migration from skin (or related tissues) usually occurs after contact with an antigen, and accompanies maturation. Maturation is another functional activity of dendritic cells.

As used herein, the term "dendritic cell maturation" and its variants relates to the phenotypic changes the dendritic cell undergoes, and the role it plays in activating T lymphocytes. Accordingly, the term maturation includes, but is not limited to, upregulation of MHC, expression of certain accessory and activation molecules, such as CD80/B7-1, CD86/B7-1, CD54/immune cell adhesion molecule- 1 (ICAM-1), and CD25/interleukin-2 (IL-2) receptor. Another indication of dendritic cell maturation is the ability to process and present antigen to antigen specific, syngeneic T lymphocytes. Yet another indication of dendritic cell maturation is the ability to stimulate proliferation of allogeneic T lymphocytes. Still another indication of dendritic cell maturation is the ability to conjugate to T lymphocytes, particularly memory T lymphocytes.

It has been found that if explants of mouse (Larsen et al., 1990) or human skin (Richters et al., 1994) are placed in organ culture, dendritic cells selectively migrate into the medium surrounding the explant. The present invention relates in part to the discovery that this system actually relates to the in vivo functional activity of dendritic cells. In particular, in vitro skin organ cultures can be used to further characterize dendritic cell migration, and to provide access to cutaneous dendritic cell function and activity in disease states. An example is HIV-1 infection. Dendritic cells are found in the epithelia covering all of the organs involved in the sexual transmission of HIV-1 (Nestle et al., 1994), making their susceptibility to HIV-1 of importance to study.

The present invention relates, in part, to discoveries made in the course of setting up organ cultures of normal human skin. Specimens were removed with a dermatome from skin that would otherwise have been discarded following plastic surgery. When the explants were placed in culture, dendritic cells emigrated and exhibited a characteristic morphology, phenotype, and T cell stimulatory function. Unexpectedly, in addition to the dendritic cells, the inventors herein have discovered that cutaneous TcR $\alpha\beta^+$ T cells also emigrate, making both T cells and dendritic cells accessible in a highly enriched form for study. Prior to the present invention, conjugation of cutaneous dendritic cells and T lymphocytes had not been observed. Most T cell emigrants from murine skin explants expressed the $\gamma\delta$ T cell receptor phenotype, and did not appear to interact with dendritic cell emigres. Several properties of these T cells, including their ability to form distinctive conjugates with autologous dendritic cells, are described in the Examples, infra.

The interaction of dendritic cells with these cutaneous T cells represents a microenvironment that is believed to be critical for immune, inflammatory, and infectious diseases, particularly in skin and related mucous membranes. For example, the interaction of dendritic cells with cutaneous T cells may perform an important function in autoimmunity. This interaction is also believed to be significant in chronic inflammation, e.g., associated with psoriasis, mycosis fungoides, etc. This unique interaction of dendritic cells with cutaneous T cells appears to be critical for immune responses in contact allergy, atopic dermatitis, skin grafting, and in viral infection.

In particular, the invention relates as well to discoveries made in pursuit of the role of dendritic cells in HIV-1 pathogenesis, which discoveries hinged on the in vitro assay system described herein. The investigation of HIV-1 pathogenesis requires consideration of dendritic cells within human skin. In contrast to the cultured blood dendritic cells used in prior studies, skin dendritic cells (Langerhans cells) express more of the CD4 receptor (Wood et al., 1983), and therefore may be more susceptible to direct infection with HIV-1. Skin dendritic cells are known to interact with T cells in situ, e.g., within the dermis during antigen-elicited recall reactions (Kaplan et al., 1987). Finally, skin is a model for the external linings of organs involved in the sexual transmission of HIV-1 (Miller et at., 1993), and dendritic cells are found in oral, anal, vaginal, and cervical epithelia (Daniels, 1984; Miller et al., 1992b).

The Examples disclosed herein concerning HIV-1 infection in normal skin reveal that the cells prove remarkably permissive to HIV-1 infection even though no exogenous mitogens, lymphokines, or foreign sera were be applied. The milieu for this productive infection ,with HIV-1 is not free dendritic cells or T cells, but instead unique conjugates of dendritic cells and T cells bearing the memory phenotype. This cellular environment appears to be important in sexual transmission of HIV-1, the chronic production of virus, and the relentless loss of memory T cells. This surprising discovery forms the basis for the present method of identifying agents capable of preventing or inhibiting HIV infectivity, both acute infection and transmission, and the chronic destruction of memory T cells.

Preferably, the assay of the invention is performed with human skin. However, the invention contemplates use of skin from other mammals, particularly non-human primates (which are important in the study of HIV) and swine.

Assay Methods

The methods of the present invention generally involve analyzing the effect of an agent to be tested on the functional activity dendritic cells from skin explants. The agent can be administered to the skin explant prior to organ culture. As discussed above, the behavior of dendritic cells in skin is related to their behavior in similar tissues, notably mucous membranes. Human skin may be readily obtained, e.g., from dermatological procedures or plastic surgery. In contrast, human mucous membrane tissue is not easily obtained.

Preferably, the test and control skin explants are the same size, i.e., have the same surface area. This ensures that the functional activity measured for the cells in culture fluid is normalized between the control and test cultures. Alternatively, however, results can be normalized to a representative skin explant size.

The culture medium can be any culture medium compatible with dendritic cells and lymphocytes. Preferably, the culture medium is RPMI 1640 supplemented with buffer salts, e.g., HEPES, 2-mercaptoethanol, antibiotics, glutamine, and serum. Preferably, the serum is normal human serum at a 10% concentration. The skin explants are treated to sterilize them, preferably by washing with $Ca^{++}$ and $Mg^{++}$-free phosphate buffered saline (PBS), and incubating with gentamycin prior to culturing. The explants are floated skin side down in a 37° C. humidified incubator. The $CO_2$ level can be maintained at between about 5–10%. After 2–5 days in culture, the skin can be removed and the presence of emigres detected in the culture medium. Preferably, the cultures are treated with an enzyme, such as collagenase D, to facilitate harvesting of the cells and to prevent losses of cells due to trapping within collagenous debris.

In a particular embodiment, an agent can be applied to a skin explain, either prior to or after excision from the donor. The explant is then floated dermal side down in culture fluid. This strategy models the effects of applying a therapeutic gel, cream, foam, lotion, or ointment to skin or mucous membranes topically in a subject.

Alternatively, the agent to be tested can be dissolved or suspended in the culture fluid itself. This technique relates both to agents that could be applied topically, and to agents that may be administered systemically. Systemic administration can be effective both to prevent the activation of dendritic cells present in skin or mucous membrane, or to prevent activity of dendritic cells that have migrated from skin or mucous membrane.

The method of determining whether an agent modulates dendritic cell functional activity requires determining the degree of functional activity of dendritic cell emigrants from the explant is an assay sample compared with a control sample. Any difference in functional activity between the assay sample and the control sample indicates that the agent modulates dendritic cell functional activity.

In a first embodiment, the number of dendritic cells that migrate can be determined. This determination can be made by counting dendritic cells that have migrated from the skin explant into the culture medium. Dendritic cells may be identified by light microscopy based on their size (dendritic cells are relatively large, compared with lymphocytes), unique morphology (extension and retraction of lamellipodia or veils), and motility (bending of the lamellipodia). Dendritic cells constantly push out processes without moving; however, each process bends and flails in the medium.

Alternatively, dendritic cells can be identified by detecting the presence of specific markers, including but not limited to class II major histocompatibility antigens (MHC), termed human leukocyte antigens (HLA) in humans. For example, human dendritic cells carry HLA-DR, HLA-DQ, etc. In specific examples, infra, dendritic cells are identified by immunolabeling with HLA-DR-specific antibodies. Other dendritic cell markers include, but are by no means limited to, CD1a, and low expression of CD14 and T cell/natural killer cell markers, such as CD16.

As described in the examples, infra, dendritic cell emigrés are frequently conjugated to T lymphocytes. Such T lymphocytes can be identified using light microscopy by their small size relative to the dendritic cell. Alternatively, T lymphocytes can be identified by detecting the presence of T cell markers, e.g., by immunostaining. Specific markers for T lymphocytes include, but are not limited to, CD2, CD3, CD4/CD8, CD45RO, LFA-3, and the T cell receptor (TcR) $\alpha\beta$ or TcR$\gamma\delta$.

An important measure of dendritic cell functional activity is the ability to associate with T lymphocytes, as observed in the Examples, infra. As noted, this activity can be observed with light microscopy, by observing the presence of one to four or more small, round lymphocytes conjugated to a larger, morphologically distinct, dendritic cell. Alternatively, the dendritic cell-T lymphocyte conjugates can be detected by immunofluorescence (microscopy or FACS), by detecting the presence on a single conjugate that decorates or labels with both dendritic cell and T lymphocyte markers.

Dendritic cell maturation can be detected by measuring increased levels of expression or upregulation of certain accessory and regulation molecules on dendritic cells, e.g., MHC, CD80, CD86, CD54, and CD25. These markers can be detected immunologically, biochemically, or a combination thereof.

Immunological detection can be performed using standard techniques, including but not limited to cellular ELISA, whole cell lysate ELISA (e.g., International Patent Publication WO 92/08981, published May 29, 1992), immunohistology, fluorescence microscopy, and cytofluorography (i.e., analysis on a fluorescence activated cell sorting [FACS] apparatus). In a specific embodiment, both dendritic cells and T cells are detected by FACS analysis and by immunostaining under light microscopy, i.e., immunohistology.

In a further embodiment, the functional activity of dendritic cells can be measured in a T cell proliferation assay. In one aspect, an allogeneic proliferation assay can be performed, in which the dendritic cells are mixed with allogeneic T cells (i.e., T cells from a non-MHC-matched individual). Generally, mature dendritic cells are effective in stimulating proliferation of allogeneic T cells (Steinman and Inaba, "Stimulation of primary Mixed Leukocyte Reaction," CRC Critical Reviews in Immunol. 5: 331–348, 1985).

Alternatively, the ability of dendritic cells to process and present antigen to antigen specific T cell lines or clones can be measured. For an antigen presentation assay, autologous or syngeneic T lymphocytes should be used, to avoid an allogeneic response. Preferably, the dendritic cells are irradiated, e.g., with 1500–1600 rads, to ensure that any profilerative response that is detected results from T cell proliferation. However, this is not critical, as dendritic cells do not usually proliferate with abandon.

In another aspect, the ability of dendritic cells to present superantigens can be evaluated (see, e.g., Bhardwaj et al., 1994). Superantigens may be critical compounds of infectious agents and immune conditions, including HIV and psoriasis.

In a further aspect, the present invention provides an advantageous system for evaluating superantigens. In vitro, dendritic cells process and present small, and presumably physiologically relevant, levels of super antigen (Bhardwaj et al., 1993). Thus, the dendritic cell-T lymphocyte emigrés can serve as a physiologically relevant assay system for evaluating the potency and effects of superantigens.

Using techniques that are well known in the art, T lymphocyte activation, e.g., proliferative responses, can be measured in vitro. In a specific embodiment, infra, T cell responses are detected by measuring incorporation of $^3$H-thymidine, which increases with DNA synthesis associated with proliferation. Cell proliferation can also be detected using an MTT assay (Mossman, 1983, J. Immunol. Methods 65: 55–63; Niks and Otto, 1990, J. Immunol. Methods 130: 140–151). Stimulation can be determined by increased expression of cellular markers on the T cells, such as interleukin 2 receptor, LFA-3, etc. Similarly, lymphokine production assays can indicate T cell proliferation. Generally, production of lymphokines is detected immunologically, most frequently by ELISA. However, lymphokine production can be assayed using co-stimulation assays (see, e.g., Birkeland et al., 1987, J. Exp. Med. 166: 506 [IL-4 assay]; Fehlner et al., 1991, J. Immunol. 146: 799–806 [CTLL co-stimulation assay for IL-2]; Mossmann et al., 1986, J. Immunol. 136: 2348) or using the ELISPOT technique (Czerkinsky, et al., 1988, J. Immunol. Methods 110: 29). Alternatively, mRNA for lymphokines can be detected, e.g., by amplification (see Brenner, et al., 1989, Biotechniques 7: 1096)or in situ hybridization (see, e.g., Kasaian and Biron, 1989, J. Immunol. 142: 1287).

Detection of the Presence of HIV Infected Cells

The method of the invention specifically related to identification of agents that can inhibit or prevent HIV infection of dendritic cells, or transfer of HIV from infected dendritic cells to memory T cells, relies on detecting the presence and productivity of HIV infection. Infection of the in vitro skin explant cultures is assayed by contacting the cultures with HIV isolates. HIV isolates can be obtained from the NIH AIDS Research and Reference Reagent Program, operated by Ogden BioServices Corporation, 684 Lofstrand Lane, Rockville, Md. 20850. Primary HIV isolates are also available from HIV-positive individuals and people with AIDS. Alternatively, cells infected with HIV, rather than free isolates, can be used to infect assay cultures of the invention.

HIV can be detected in cells by many techniques, including the presence of HIV mRNA or DNA, the presence of HIV antigens in cells or in the culture fluid, and the presence of HIV virions themselves. Many of these techniques also provide for determining the productivity of an HIV infection, which is a measure of activity and virulence.

The presence of HIV mRNA or integrated DNA is preferably detected using polymerase chain reaction (PCR) (Cameron et al., 1992; Saksela et al., 1994). For example, HIV mRNA can be detected by reverse transcriptase-initiated PCR (see, e.g., Saksela et al., 1993, J. Virol. 67: 7423–27). PCR can be carried out, e.g., by use of a Perkin-Elmer Cetus thermal cycler and Taq polymerase (Gene Amp™, Boehringer Mannheim). The amplified PCR products can be detected by incorporation of radiolabeled nucleotides, endlabeling, e.g., with $\gamma^{32}$P-ATP, or by staining with ethidium bromide. However, according to the present invention, radiolabels are preferred as these can yield more quantitative information, e.g., by analysis of band density after gel electrophoresis and autoradiography. Virus (provirus) copy number can be determined by comparison of the intensity of the PCR band with a standard, such as the latently infected cell line ACH-2, which contains one copy of provirus in each cell (Folks et al., 1986). In a specific embodiment, infra, PCR of the vital gag sequence is used. Both the presence of HIV and its level of activity can be determined by analysis of mRNA. For quantitation of the level of HIV mRNA, after gel electrophoresis and autoradiography, the intensities of mRNA signals can be compared with those of the control RNAs analyzed in parallel to estimate the approximate amounts of HIV-specific mRNAs present in the samples. The amount of viral mRNA corresponds to the level of viral activity (see, e.g., Saksela et al., 1994).

Alternatively, the presence of HIV can be determined by an assay for reverse transcriptase. Reverse transcriptase can be detected immunologically, using an antibody to the enzyme. Preferably, reverse transcriptase is detected using an enzyme activity assay, e.g., as described in Cameron et al. (1992).

HIV infection of cells and the productivity of infection can also be detected by detecting the presence of HIV antigens, i.e., HIV proteins (including reverse transcriptase). In a specific embodiment, infra, the presence of p24 antigen is indicative of infection with HIV. p24 antigen can be detected immunologically, e.g., at the single cell level with the monoclonal antibody produced by hybridoma 183, clone H12-5C (Chesebro et al., 1992), or in the culture fluid using a p24 detection kit (e.g., New England Nuclear kit #NEK-060B).

In another embodiment, the presence and quantity of HIV can be detected by electron microscopy (see, e.g., Stossel et al., 1990). In particular, vital buds can be observed on the surface of infected cells, and free in proximity to infected cells.

In yet another embodiment, productive HIV infection can be detected by the presence of dendritic cell-T lymphocyte syncytia. Syncytia can be detected under light microscopy, by immunostaining for the presence of dendritic cell and T lymphocyte markers on the syncytia. In a specific example, infra, syncytia stain for both MHC class II antigen (a dendritic cell phenotype) and CD3 (a T lymphocyte phenotype); some stained moderately for CD1a.

Agents That Modify Dendritic Cell Activity

Any agents can be tested for the ability to modulate dendritic cell functional activity. Such agents may be effective to prevent HIV acute or chronic infection as well. For example, an agent that prevents conjugation of dendritic cells to T cells may prevent the initial infection by HIV, and also prevent infection of memory T cells by infected cutaneous dendritic cells.

Although not intending to be limited to any particular agent or mode of operation, the present invention contemplates testing of a number of agents, including, but not limited to, cytokines, non-steroidal anti-inflammatory agents, steroids, antiviral compounds (nucleotide analog-type inhibitors of the reverse transcriptase, such as but not limited to AZT (zidovudine, Retrovir), 2',3'-dideoxy-inosine (ddI, Videx), 2',3-dideoxycytidine (ddC, zalcitabine, HIVID), 3TC (Lamivadine), d4T (Stavudine), FLT, and PMEA; non-nucleotide analog inhibitors of reverse transcriptase, such as Nevirapine (BI-RG-587), TIBO (R82913), pyrinodes (such as R-697,661 and L-696,227), bis(heteroary)piperazines (BHAPs, such as U-87201E and U-90,152), atevirdine mesylate (ATV) and R-89431; HIV protease inhibitors, include substrate analogs and non-analogs, such as Ro 31-8959, A-77003 and A-80987; HIV Tat protein inhibitors, such as Ro 5-3335 and Ro 27-7429; blockers of viral entry into cells, such as soluble CD4 protein (sCD4), and chimeric sCD4 derivatives, such as CD4-IgG and CD4-PE40; blockers of HIV RNaseH activity, such as the AZT derivative azidothymidine monophosphate; drugs that alter the intracellular milieu to create conditions less favorable for vital replication, such as the free-radical scavengers and glutathione-level restoring drugs (N-acetylcysteine and similar drugs), and thalidomine (which seems to lower blood TNF-α levels)), antibiotics (such as gramicidin), analogs or inhibitors of leukocyte adhesion molecules (e.g., CD80 and CD54), antibodies to leukocyte adhesion molecules, oligosaccharides, polysaccharides, glycosaminoglycans (e.g., hyaluronic acid, chitosan, pentosan polysulfate, alginate, and the carbohydrate portions of the proteoglycans heparin, keratan sulfate, chondroitin sulfate, heparan sulfate, dermatan sulfate, and the like), proteoglycans, charged high molecular weight carbohydrates (e.g., dextran sulfate), to mention but a few, can be assayed according to the methods of the present invention.

Therapeutic Methods and Compositions

According to the invention, agents that may be identified through the methods disclosed herein can be prepared as pharmaceutical compositions for administration to an individual believed to be in need of such treatment. For example, an agent that inhibits maturation, but not the migration, of dendritic cells from skin or related tissues may be desirable for the treatment of contact allergy. An agent that inhibits formation of dendritic cell-T lymphocyte conjugates may block immune responses and viral infection, particularly HIV infection.

Accordingly, the invention provides suitable pharmaceutical compositions for use in the treatment of an immunological disease or disorder, or infection with HIV. A composition comprising "A" (where "A" is a single molecule, such as a protein) is substantially free of "B" (where "B" comprises one or more contaminating proteins, or other contaminants, but not including racemic forms of A) when at least about 75% by weight of the composition is "A". Preferably, "A" comprises at least about 90% by weight of the A+B species in the composition, most preferably at least about 99% by weight. It is also preferred that a composition, which is substantially free of contamination, contain only a single molecular weight species of each of the defined components having the activity or characteristic of interest.

Preferably, such compositions comprise the modulating agent and a pharmaceutically acceptable carrier or excipient. The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The agent should be administered in a therapeutically effective amount to the subject in need of treatment. The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host. In a specific embodiment, the therapeutically effective amount of an agent is an amount sufficient to modulate dendritic cell activity in treatment target area.

The present invention may be better understood by reference to the following non-limiting Examples, which are provided as exemplary of the invention.

EXAMPLE 1

BOTH DENDRITIC CELLS AND MEMORY T LYMPHOCYTES EMIGRATE FROM ORGAN CULTURES OF HUMAN SKIN AND FORM DISTINCTIVE DENDRITIC-T CELL CONJUGATES

Prior studies of mouse skin in organ culture have shown that dendritic cells selectively emigrate from the explants over 1–3 days. This emigration models the movements of dendritic cells that can occur in situ, as in transplantation and contact sensitivity. In this Example, we cultured explants of normal human skin that had been removed with a dermatome. Dendritic cells with characteristic morphology and MLR stimulatory activity emigrated from the skin explants. The dendritic cells had the expected phenotype, i.e., rich in MHC class II and accessory molecules like B7-1, ICAM-1, and LFA-3. Small lymphocytes also were present in the emigrated populations and proved to be T cells exclusively, almost entirely of the TcR $\alpha\beta$ and memory (CD45RA$^{weak}$, CD45R0$^+$, LFA-3/CD58$^+$) type with a CD4: CD8 subset ratio of about 2:1. Some of the T cells were tightly bound to the dendritic cells. These conjugates did not dissociate following exposure to trypsin or calcium and magnesium free medium, or during cytofluorography. This made it possible to sort distinct populations of single dendritic cells, single T cells, and conjugates of the two cell types. Conjugates would continue to form from mixtures of separated dendritic cells and T cells in culture. Therefore, cutaneous dendritic cells and memory T lymphocytes emigrate from human skin explants, and some of these cells form distinctive conjugates that contribute to immunologic recall reactions.

Materials and Methods

Culture Medium

RPMI 1640 (Cellgro, Fisher Scientific, Springfield, N.J.) was supplemented with 10 mM HEPES, 50 µM 2-mercaptoethanol, 100 U/ml Penicillin—100 µg/ml Streptomycin, 2 mM L-glutamine, and either 10% fetal calf serum (FCS, Gibco BRL) or 10% normal human serum (NHS, obtained from lab donors).

Preparation of Cell Suspensions

Split thickness, normal, breast or abdominal skin was removed with a dermatome following cosmetic surgery. The skin was washed twice-with sterile Ca$^{++}$ and Mg$^{++}$-free PBS, incubated in medium with 200 µg/ml Gentamicin (Gibco BRL) for 1 hr at 4° C., washed twice in sterile Ca$^{++}$ and Mg$^{++}$-free PBS, and floated as 3×3 cm explants dermal side down, each in 15 ml of medium in 100 mm dishes (#3003, Falcon, Oxnard, Calif.). After 2–5 days at 37° C., the skin was removed and the debris digested with 400 units/ml Collagenase D (#1088 882, Boehringer Mannheim [BM], Indianapolis, Ind.) for 1 hr at 37° C. This was essential to be able to harvest the cells without marked losses due to trapping within collagenous debris. The cells were pooled, washed in medium, and the numbers of viable cells (>95%) assessed by Trypan blue (Gibco BRL) exclusion. Skin cells also were prepared from epidermal sheets and dermal explants as described (Lenz et al., 1993; Romani et al., 1989), except that the dendritic cells were enriched by floatation on 13.5% metrizamide (Kripke et al., 1990).

Immunolabeling and Cell Sorting

To greater than 2×10$^4$ skin cells/well of a 96 well V-bottomed tray (Flow/ICN), 100 µl of the appropriate dilution of primary monoclonal antibody (Table I, Results) was added for 30 min at 4° C. The cells were washed 4 times in PBS containing 5% FCS and 10 mM azide, exposed to FITC-conjugated F(ab')$_2$ fragment goat anti-mouse IgG (Cappel Research Products, Durham, N.C.) 30 min at 4° C., washed, incubated in 1% normal mouse serum 5–15 min at 4° C., exposed 30 min to PE-conjugated anti-HLA-DR (to identify MHC class II rich dendritic cells; Becton Dickinson Immunocytometry Systems, Inc. [BDIS], San Jose, Calif.), washed, fixed in 10% formalin 10 min, washed, and analyzed on a FACScan (BDIS). The controls for nonspecific Ig binding (FITC channel) was nonreactive IgG$_1$, IgG$_{2a}$, or IgG$_{2b}$ (Sigma Chemical Co.) and PE-conjugated IgG$_{2a}$ (BDIS). As described in Results, skin cell suspensions could be sorted into dendritic cells, T lymphocytes, and dendritic cell-T cell conjugates using a FACStar$^{PLUS}$ (BDIS) with laser excitation of 200 mW at 480 nM (Innova 90-5 Argon laser, Coherent, Inc., Palo Alto, Calif.).

Light Microscopy of Cytospin Smears

Fifty µl of skin cells (4×10$^5$/ml) were cytospun onto precleaned microscope slides (Baxter Diagnostic Inc., Parkway, N.J.) using a Shandon Cytocentrifuge (Shandon Inc., Pittsburgh, Pa.). The slides were immediately removed from the holders, air dried 1 hr, fixed in acetone (Fisher Scientific, Fair Lawn, N.J.) 10 min at room temperature, air dried, rehydrated with Tris buffered saline (TBS, pH 7.4) and incubated with anti-CD3 (Leu 4), anti-CD4 (Leu 3a), ami-CD5 (Leu 1), anti-CD8 (Leu 2), or anti-HLA-DR (9.3C9, HB180) for 30–60 min in a humidified atmosphere at room temperature. The cytospins were washed 4X with TBS, exposed to HRP-conjugated F(ab')$_2$ donkey-anti-mouse IgG (Jackson ImmunoResearch Laboratories, Inc., West Grove, Pa.) 30–60 min, washed, exposed to the HRP substrate diaminobenzidene (DAB; prepared according to manufacturer's instructions; Polysciences Inc., Warrington, Pa.) for 10–30 min, and washed with distilled water. Cytospins could be stained with Giemsa (Fisher Scientific, Pittsburgh, Pa.) prior to coverslipping with a PBS/Glycerol mix (Sigma), and photography on a Nikon Optiphot Microscope (Morell Instrument Co. Inc., Melville, N.Y.).

T Cell Proliferative Responses

The MLR stimulating activity of skin emigrés was assessed in cultures of $1.5 \times 10^5$ allogeneic T cells in triplicate as described (O'Doherty et al., 1993). To detect T cell proliferation in the emigrés themselves, $4 \times 10^4$ cells in 96 well round bottomed microtest trays (Flow/ICN, Hotsham, Pa.) were cultured±human rIL-2 (#799 068, BM) or Concanavalin A (ConA 3 µg/ml, BM). Proliferation was monitored either by $^3$H-thymidine uptake or by staining cytospins of the cultures with the monoclonal MIB-1 antibody to the Ki-67 nuclear antigen (AMAC, Inc. Westbrook, Me.) that is expressed in cycling cells.

Results

Preliminary experiments were carried out using standard epidermal and dermal cell suspensions (Lenz et al., 1993; Romani et al., 1989). Typical epidermal and dermal dendritic cells and some small lymphocytes were noted. However, the large majority of keratinocytes prompted us to explore a biological feature to isolate dendritic cells, i.e., dendritic cells emigrate selectively from organ cultures of skin (Larsen et al., 1990).

Skin Emigrés Contain Potent Immunostimulatory Cells

When normal skin was removed with a dermatone and cultured, many cells emigrated into the medium within a day and for several days thereafter. Large dendritic cells were abundant, but there were many small lymphocytes as well. The average yields of leukocytes were 57,000±6200 cells/per cm$^2$ (mean±SEM from the first 13 experiments). This value was comparable to the yield obtained when separated epidermis and dermis were dissociated by standard methods (26,200±6504 epidermal and 25,900±9712 dermal leukocytes/cm$^2$ of skin; mean±SEM from 11 experiments). However, skin emigrés were >95% viable and had few contaminating keratinocytes, while dissociated cells had many dead cells and an overwhelming majority of keratinocytes. When cryosections of the skin explants were stained for dendritic cells (anti-CD1a and anti-HLA-DR) before and after 4 days of culture large numbers remained in the explant. Nevertheless, when pieces of skin were replated into fresh medium after 4 days of culture, few additional cells emigrated, implying that an initial stimulus for the emigration had subsided (Discussion, infra).

Figure 1B:
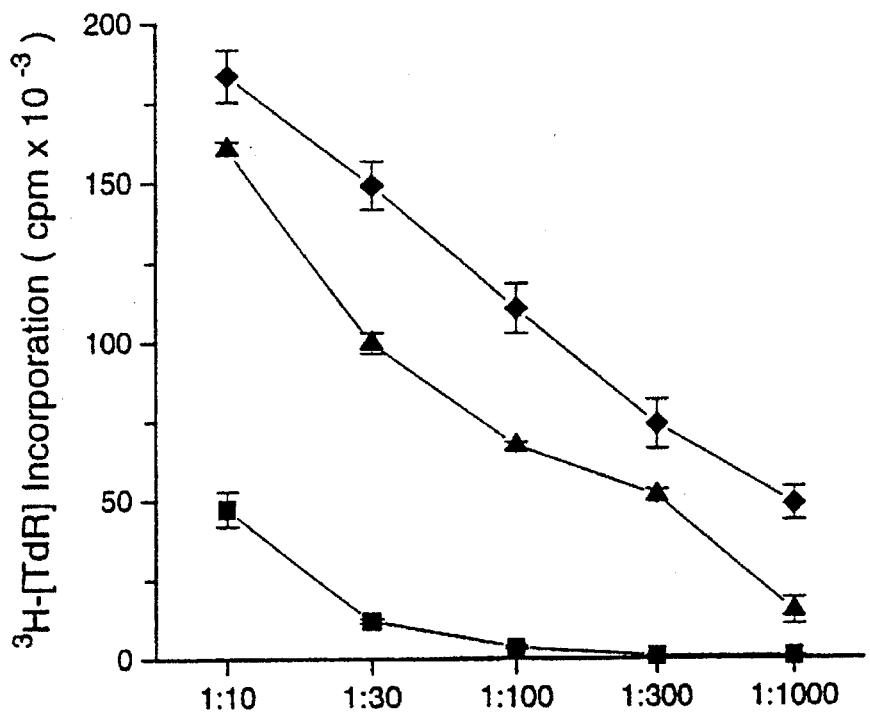

The emigrated populations were potent stimulators of the primary MLR (30–100 X more potent than blood cells), much like skin-derived dendritic cells prepared by standard methods (FIG. 1; compare A and B and (Nestle et al., 1994; Sontheimer, 1985)).

Light Microscopy of the Emigrated Cells

Live emigrated cells were examined at 37° C. in an inverted phase contrast microscope. The dendritic cells extended large sheet-like processes ("veils") in several directions. These processes formed and retracted continually. Some of the small round lymphocytes bound to the dendritic cells (one to three T cells per dendritic cell, but usually one). The conjugates were stable for hours, and we could not dissociate them with trypsin (0.25% for 5 min, 37° C.) or Ca$^{++}$ and Mg$^{++}$ free Hanks (1 mM EDTA and 1% BSA, 4° C.).

The emigrés were cytospun onto slides and stained with monoclonals. The dendritic cells were strongly MHC class II positive, and the lymphocytes CD3$^+$ (FIGS. 2a, b). Both CD8$^+$ (not shown) and CD4$^+$ lymphocytes were noted, either free or attached to the dendritic cells (FIG. 2c).

Phenotype of Migrating Leukocytes by Cytofluorography

Skin emigrés were stained with a panel of antibodies and FITC-goat anti-mouse Ig, and counterstained with PE-anti-HLA-DR to identify dendritic cells. FACS profiles from one of three similar experiments are in FIG. 3, while a summary of fluorescence intensities on three experiments is in Table 1.

TABLE 1

Cell Surface Antigens of Skin Emigrés Monoclonal Antibody

| Specificity | Isotype | Source/Name | Dendritic cells | T cells |
|---|---|---|---|---|
| MHC | | | | |
| HLA-DR | IgG$_{2a}$ | BDIS | ++++ | + |
| HLA-DQ | IgG$_1$ | ATCC/HB103 | +++ | +/− |
| HLA-DP | IgG$_{2a}$ | Gift-S. Y. Yang/PL-15 | +++ | +/− |
| HLA-A,B,C | IgG2a | ATCC/HB95 | ++++ | ++++ |
| CD74/Ii | IgG$_1$ | Serotec | − | − |
| T CELL | | | | |
| CD2 [LFA-2] | IgG$_1$ | ATCC/HB195 [TS2/18] | + | +++ |
| CD3 | IgG$_1$ | Gift-R. Evans/Leu 4 | − | ++++ |
| CD4 | IgG$_1$ | Gift-R. Evans/Leu 3a | ++ | +++ |
| CD5 | IgG$_1$ | Serotec | +/− | ++++ |
| CD7 | IgG$_1$ | Serotec | − | ++++ |
| CD8 | IgG$_1$ | BDIS/Leu 2 | − | ++++ |
| TcRαβ | IgG$_1$ | BDIS | − | +++ |
| TcRγδ | IgG$_1$ | BDIS | − | − |
| LINEAGE | | | | |
| CD1a | IgG$_1$ | ATCC/CRL8020 [OKT6] | +++ | − |
| CD13 | IgG$_1$ | Dako/M812 | ++ | − |
| CD14 | IgG$_{2b}$ | ATCC/TIB228 [3C10] | + | − |
| CD33 | IgG$_{2a}$ | M195$^a$ | ++ | − |
| CD19 | IgG$_1$ | Amac 1283 | − | − |
| FcγR/C3R | | | | |
| CD16 | IgG$_1$ | 3G8 | − | − |
| CD32 | IgG$_{2b}$ | ATCC/HB217 | ++ | − |
| CD64 | IgG$_1$ | ATCC/HB9469 | + | − |
| CD21 | IgG$_{2a}$ | ATCC/HB135 | − | − |
| CD45 | | | | |
| CD45 | IgG$_{2a}$ | ATCC/HB196 | +++ | +++ |
| CD45RA | IgG$_{2a}$ | R. M. Steinman/4G10 | + | + |
| CD45RO | IgG$_{2a}$ | UCHL-1$^b$ | +++ | +++ |
| INTEGRINS/Ig ADHESINS | | | | |
| CD11a | IgG$_1$ | ATCC/HB202 [TS1/22] | + | ++ |
| CD11b | IgG$_{2b}$ | ATCC/CRL8026 [OKM1] | ++ | − |

TABLE 1-continued

Cell Surface Antigens of Skin Emigrés
Monoclonal Antibody

| Specificity | Isotype | Source/Name | Dendritic cells | T cells |
|---|---|---|---|---|
| CD11c | IgG$_1$ | UO1/521 | +++ | − |
| CD29 | IgG$_1$ | Serotec | ++ | ++ |
| CD31 [PECAM] | IgG$_{2a}$ | HEC-7$^c$ | ++ | − |
| CD54 [ICAM-1] | IgG$_1$ | 84H10$^d$ | ++ | + |
| CD58 [LFA-3] | IgG$_1$ | ATCC/HB205 | +++ | ++ |
| ACTIVATION ANTIGENS | | | | |
| CD25 [IL2R] | IgG$_1$ | AM47 | ++ | + |
| CD40 | IgG$_1$ | Biosource CT-CD40 | +++ | + |
| CD80 [B7-1] | IgG$_1$ | BDIS | +++ | + |

*Results are tabulated for the majority of the emigrated dendritic cells and T cells according to the formula: +, <1X background; ++, 1-10X background; +++, 10-100X background; ++++, >100X background.
$^a$Scheinberg, D. A., M. Tanimoto, S. McKenzie, A. Strife, L. J. Old, and B. D. Clarkson. 1989. Monoclonal Antibody M195: A Diagnostic Marker for Acute Myelogenous Leukemia. Leukemia 3:440–445.
$^b$Smith, S. H., M. H. Brown, D. Rowe, R. E. Callard, and P. C. L. Beverley. 1986. Functional subsets of human helper-inducer cells defined by a new monoclonal antibody, UCHL1. Immunol. 58:63–70.
$^c$Muller, W. A., C. M. Ratti, S. L. McDonnell, and Z. A. Cohn. 1989. A human endothelial cell-restricted, externally disposed plasmalemmal protein enriched in intercellular junctions. J. Exp. Med. 170:399–414.
$^d$Makogoba, M. W., M. E. Sanders, G. E. Ginther Luce, M. L. Dustin, T. A. Springer, E. A. Clark, P. Mannoni, and S. Shaw. 1988. ICAM-1 a ligand for LFA-1-dependent adhesion of B, T, and myeloid cells. Nature 331:86–88.

Figure 3:
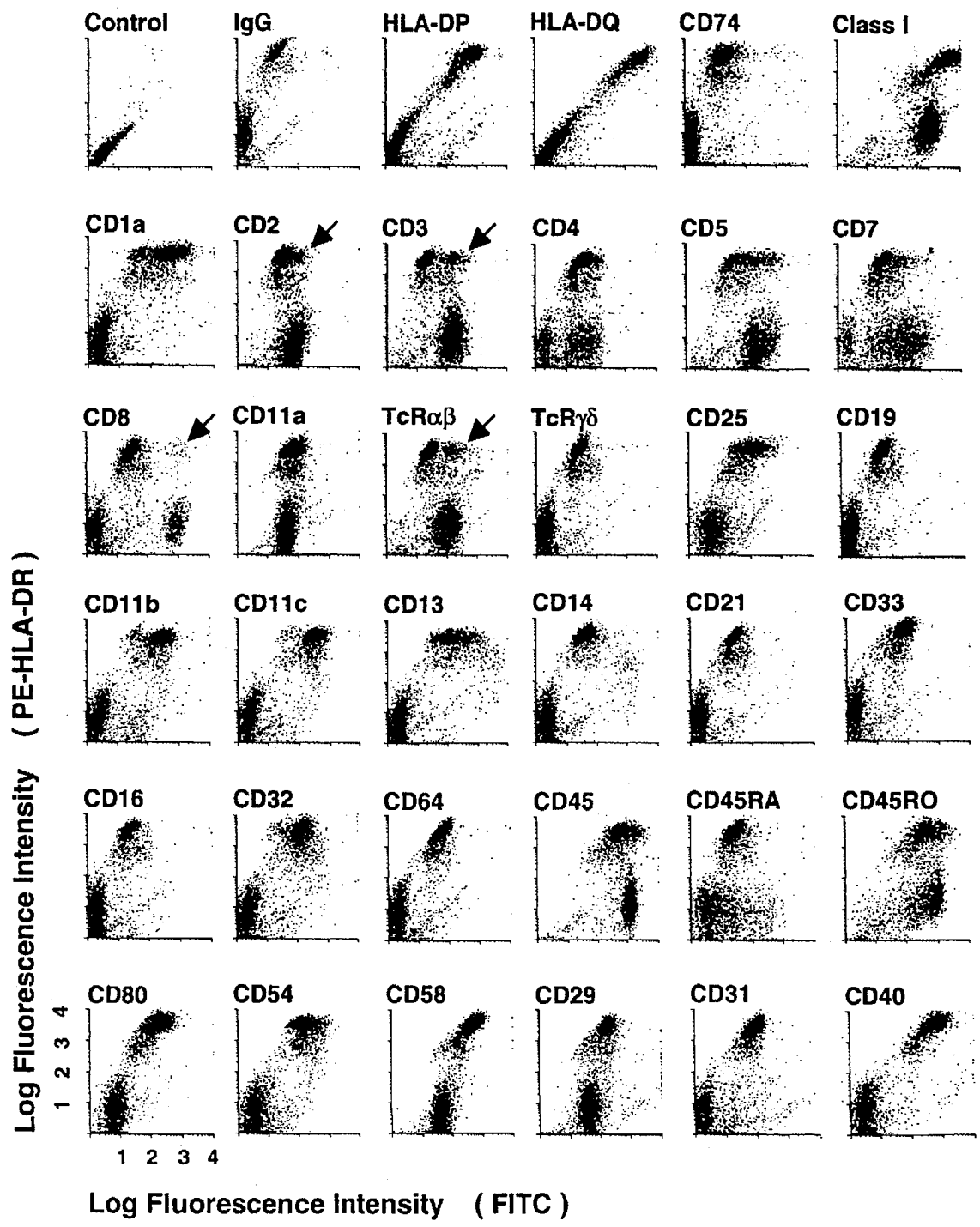
FIG. 3 Two color immunolabeling of the migrants from human skin explants. One color (PE-channel, ordinate) is HLA-DR staining to identify dendritic cells. The second color (abscissa) is produced by applying a monoclonal antibody as indicated followed by FITC anti-mouse Ig. The Control panel shows cells stained with nonreactive mouse IgG, FITC anti-mouse Ig, and nonreactive, PE-labeled, isotype matched antibody. The IgG panel is the staining of cells incubated with nonreactive mouse IgG, FITC anti-mouse Ig, aM PE-HLA-DR. These panels demonstrate the background fluorescence of the strongly DR$^+$ dendritic cells. The HLA-DR$^-$ cells are not stained above the nonreactive, isotype matched, PE-control (compare first two panels). Within the DR$^+$ profiles are conjugates of dendritic cells and T cells that are highlighted by arrows in the CD2, CD3, αβ, and CD8 panels. The data are from 1 of 3 experiments, further summarized in Table 1, infra.

Skin emigrés were all CD45$^+$ leukocytes (FIG. 3). There were only rare monocytes (CD14$^+$), B cells (CD19$^+$, CD21$^+$), and NK cells (CD16$^+$). CD68$^+$ monocytes were seen in dermal suspensions as described (Lenz et al., 1993), but not in the migrants (not shown). Instead the emigrés consisted almost entirely of three groups: HLA-DR$^+$ dendritic cells, HLA-DR$^{31}$ T cells, and their conjugates.

Most HLA-DR$^−$ profiles expressed the T cell markers CD2, CD3, CD5, and CD7. The TcRs were of the αβ variety with only trace γδ cells. The ratio of CD4 to CD8 subsets was typical of blood derived cells, i.e., about 2:1. Most T cells had the memory phenotype (Smith et al, 1986), i.e., CD58/LFA-3$^+$, CD45RA$^{weak}$, CD45RO$^+$ (FIG. 3; 2nd, 3rd, 5th, 6th horizontal rows). T cell activation antigens were trace (CD25 IL2-receptor and CD80/B7-1 costimulator) or absent (HLA-DR). The T cells expressed the CD11a and CD29 integrins.

The striking finding in the FACS was the presence of profiles that were both HLA-DR$^+$ and CD3$^+$. These corresponded to the conjugates observed by light microscopy (FIG. 2) as verified by cell sorting (below). No such conjugates have been observed in cultures of blood leukocytes that are enriched in dendritic cells (not shown). Some T cell antigens (CD2, CD3, CD8, TcRαβ) separated the conjugated (arrows, FIG. 3) from the unconjugated dendritic cells. However, anti-CD4 and anti-CD5 did not provide a separation probably because CD4 (FIG. 2c asterix and (O'Doherty et al., 1993; Wood et al., 1983)) and CD5 (Wood & Freudenthal, 1992) can be expressed by dendritic cells as well as T cells. The phenotype of the T cells within the conjugates seemed identical to the T cells that had not bound to dendritic cells. Dendritic-T cell conjugates were comparable if human or fetal calf serum was present in the culture medium.

The MHC class II rich emigrés had the phenotype of mature skin dendritic cells (Lenz et al., 1993; Romani et al., 1989; Teunissen et al., 1990). There were two subsets of dendritic cells among the emigrés, the more numerous having more HLA-DR and CD1a (FIG. 3). This likely reflects the findings of Lenz et al., who showed that epidermal dendritic cells have more DR and CD1a than those from the dermis (Lenz et al., 1993). High levels of HLA-DP, HLA-DQ and Class I were expressed, but invariant chain (CD74) was absent (FIG. 3; top horizontal row). The extreme intensities of dendritic cell staining for class I and II MHC made it difficult to fully compensate the FACS instrument such that all leukocytes were displayed simultaneously on the dot blots. While CD4 and CD11 a levels looked comparable on the DR$^+$ and DR$^−$ populations, the staining of the DR$^+$ subset was much weaker when the higher autofluorescence of dendritic cells was taken into account (control and IgG panels, row 1). With the exception of CD14, dendritic cells expressed several myeloid markers: CD11b, CD11c, CD13, and CD33 (FIG. 3, row 4). The only Fcγ receptor detected was CD32; CD16 and CD64 were weak or absent (FIG. 3, row 5). Dendritic cells had high CD45R0 and low CD45RA, as is typical of activated leukocytes. Dendritic cells expressed many adhesion/activation molecules: CD80/B7-1, CD54/ICAM-1, CD58/LFA-3, CD29 β1 integrin, CD31/PECAM-1, and CD40 (FIG. 3, row 6).

Proliferative Capacity of Skin-Derived T cells

The presence of tight conjugates between dendritic cells and T cells suggested that the T cells would proliferate in culture. When dendritic cells are presenting nominal antigens, alloantigens, or superantigens, they efficiently bind and stimulate T cells in multicellular aggregates (Bhardwaj et al., 1994; Flechner et al., 1988; Pancholi et al., 1991; Pancholi et al, 1992). However, the skin cells exhibited low levels of $^3$H-thymidine uptake (Table 2). Labeling for the Ki-67 antigen (expressed in the nucleus of cycling cells) was not detected at time 0, but was detected in a fraction of the cells after 3 days of culture (Table 2). The T cells were competent to proliferate, since the mitogen ConA induced $^3$H-(TdR) uptake and Ki-67 staining that were as strong as those observed with blood mononuclear cells (Table 2). Some of the skin cell emigrants responded to IL-2 with an increased frequency of Ki-67 staining and cell size.

TABLE 2

Proliferative Response of Emigrated Cells

| | Experiment 1 | | Experiment 2 |
|---|---|---|---|
| Stimulus | Skin Cells | PBMC | Skin Cells |
| R10 | 680.6 ± 72.1 | 319.7 ± 22.9 | 1055.9 ± 163.3 |
| 10% IL2 | 3918.7 ± 120.5 | 838.7 ± 153.7 | 4254.3 ± 172.6 |
| 3 μg/ml ConA | 24,416.0 ± 1285.2 | 22,042.0 ± 1928.9 | 28,394.0 ± 680.6 |

$^3$H-[TdR] Incorporation [cpm ± SEM from triplicate cultures] by skin cells and blood cells [PBMC] after 3 days culture with various stimuli.

Isolated Dendritic Cells and T Cells Form Additional Conjugates

Figure 4A:
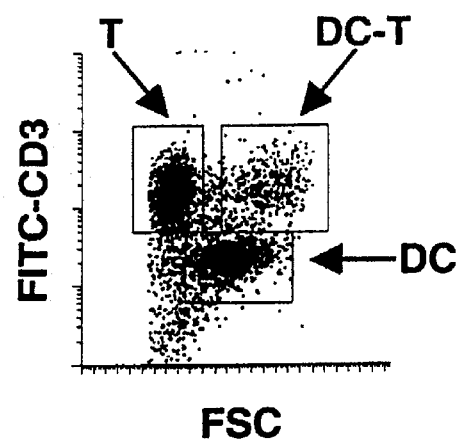
FIG. 4 Two approaches for sorting single dendritic cells (DC), single T cells (T), and dendritic-T cell conjugates (DC-T) from human skin emigrants. Strategy I: A. The suspensions are labeled directly with anti-CD3, the CD3$^+$ and CD3$^-$ fractions separated, and the CD3$^+$ cells subsequently resorted dividing the large and small fractions. Strategy II: B. The single T cells are first isolated on the basis of low forward light scatter. C. Then the T cells in the conjugates are labeled with anti-CD3 and isolated from the free dendritic cells.
Figure 4B:
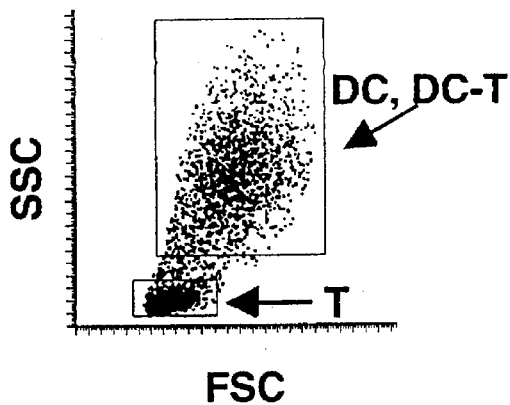
Figure 4C:
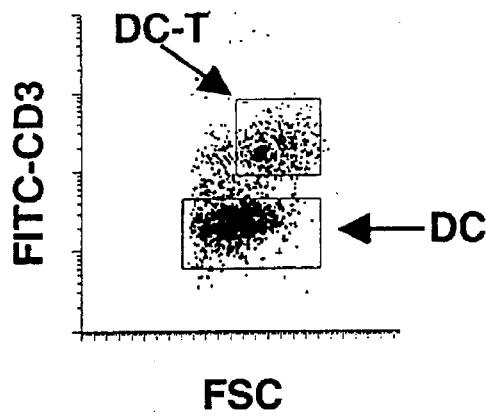

To determine if emigrated dendritic cells and T cells could form additional conjugates, we sorted the populations into free dendritic cells, free T cells, and dendritic cell-T cell couples. This was achieved using two methods (FIG. 4). In one (strategy I), the suspensions were stained with anti-CD3. Single T cells were the small (low forward scatter or FSC) and CD3$^+$, while single dendritic cells were CD3$^−$ and large. Dendritic cell-T cell conjugates were CD3$^+$ and large. In a second method (strategy II), the single T cells were not occupied by anti-CD3 but instead were collected as sin,all cells first. Then the large profiles were stained with anti-CD3 to sort the large CD3⁻ cells (dendritics) from large CD3⁺ cells (dendritic-T cell couples).

Both methods yielded 98% pure free T cells and free dendritic cells. The free T cells were small, CD3⁺ and DR⁻; the free dendritic cells, were large, CD3⁻ and DR⁺; and the conjugates contained large DR⁺, CD3⁻ dendritic cells with small, DR⁻, CD3⁺ lymphocytes (FIG. 5, note some free T cells and dendritic cells in comparable numbers disrupted from conjugates after sorting).

Figures 6A, 6B, 6C:
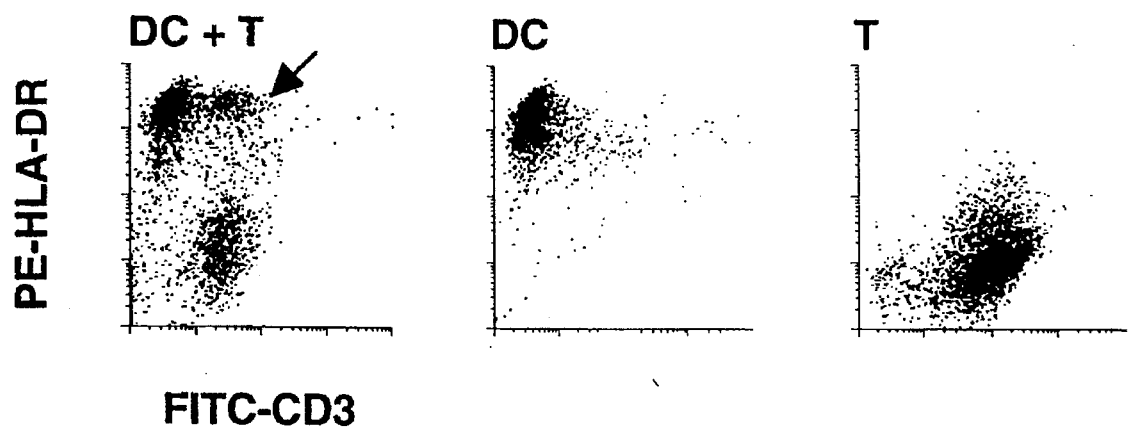
FIG. 6 Formation of dendritic-T cell conjugates following culture of sorted free dendritic cells and T cells. Dendritic-T cell conjugates were removed from skin emigrés by sorting (FIG. 4). Then the single dendritic cells (DC) and T cells (T) were cultured alone or mixed in equal numbers (DC+T). Aliquots were monitored in the hemocytometer to determine when conjugates had reformed in significant numbers, here at day 3. At this time, the suspension was harvested and stained with monoclonal antibodies for cytofluorographic analysis. A. Analysis of mixed culture of DC+T. B. Culture of single dendritic cells. C. Culture of single T cells. Newly formed conjugates were observed in A (arrow), from the dendritic cell-T cell cocultures, which were not observed with the two cell types cultured separately (B, C) Similar observations have been reproduced in at least 5 individual experiments.

Separated free dendritic cells and T cells were returned to culture. New dendritic-T cell conjugates formed after about 2, days, as assessed by direct obsevervation and by FACS studies (FIG. 6). Again most conjugates consisted of a large dendritic cell coupled to a small T lymphocyte, but sometimes two or three T cells were bound.

Discussion

The leukocyte emigration described here provides access to cutaneous dendritic cells and T cells in both normal skin and skin in several disease states. It is known that dendritic cells can be isolated from the epidermis and dermis of human skin (Cooper et al., 1987; Lenz et al., 1993; Romani et al., 1989; Teunissen et al., 1990; Tse and Cooper, 1990), although the emigration phenomenon provides these virtually free of keratinocytes in contrast to prior methods. Furthermore, memory TcRαβ⁺ T lymphocytes, which are found in skin usually at the epidermal-dermal junction (Foster et al., 1990), also emigrate when skin is explanted into culture. In mouse skin explants TcRγδ⁺ T cells emigrate (Larsen et al., 1990).

The emigration of cutaneous leukocytes has a physiologic parallel. Both dendritic cells (Knight et al., 1982; Lens et al., 1983; Pugh et al., 1983; Rhodes et al, 1989) and T cells with a memory phenotype (Mackay et al., 1990) can be found in afferent lymph suggesting that these cells move from tissue spaces into lymph channels in situ. Mackay et al. have described dendritic-T cell conjugates in afferent lymph (Mackay et al., 1989), implying that the interaction we describe in culture also can take place in situ.

The mechanism of cell emigration from skin may be characterized using the culture system described here. Perhaps explantation of skin triggers a finite release of cytokines, e.g., if contact allergens are applied to mouse skin, there is a marked upregulation of IL-1β mRNA in dendritic cells (Enk et al., 1993).

The interaction between dendritic cells and T cells to form conjugates is strong and is not disrupted during cell sorting. The specific receptors or adhesion molecules responsible for this conjugation can be studied by sorting the free dendritic cells and T cells, combining the sorted cells, and identifying monoclonals that block conjugate formation.

While some of the emigrated T cells express Ki-67 antigen after culture, we do not observe high levels of ³H-(TdR) uptake or blast formation. The behavior of the dendritic-T cell conjugates differs from the large multicellular aggregates that develop when dendritic cells are carrying known antigens or superantigens (Bhardwau et al., 1994; Fleebrier et al., 1988; Pancholi et al., 1991; Pancholi et al., 1992). The latter T cells actively proliferate and emigrate from the aggregates as lymphoblasts. Dendritic cell-T cell conjugation are very likely to contribute to cutaneous recall responses. During recall reactions (delayed type hypersensitivity), dendritic cells are juxtaposed to the mononuclear cells that constitute the DTH reaction (Kaplan et al., 1987). When epidermal dendritic cells are placed into culture, or are induced to migrate in vivo, the APCs undergo a series of changes that are termed "maturation" (,Heufler et al., 1987; Schuler and Steinman, 1985; Witruer-Pack et al., 1987). Maturation refers to the acquisition of strong T cell stimulatory activity and it is associated with the upregulation of MHC as well as accessory molecules like CD80/B7-1, CD86/B7-2, CD54/ICAM-1 (Inaba et al., 1994; Larsen et al., 1992; Larsen et al., 1990; Symington et al., 1993). Memory T cells likewise are qualitatively different from naive T cells with respect to enhanced expression of adhesion molecules like CD2, CD11a, and CD58 (Sanders et al., 1988). During explantation skin dendritic cells likely are induced to mature. The resulting changes in surface adhesion molecules then may lead to the binding of memory T cells and facilitate the response should antigen be present as in delayed type hypersensitivity reactions.

EXAMPLE 2

CONJUGATES OF DENDRITIC CELLS AND MEMORY T LYMPHOCYTES FROM SKIN FACILITATE PRODUCTIVE INFECTION WITH HUMAN IMMUNODEFICIENCY VIRUS-1

Experimentally, a productive infection with HIV-1 requires that virus be administered to T cells that are activated by mitogens. In this Example, we describe a productive milieu for HIV-1 within the confines of normal skin which does not require standard stimuli. The milieu consists of dendritic cells and T cells that emigrate from skin and produce distinctive, stable, nonproliferating conjugates. These conjugates, upon exposure to each of seven different HIV-1 isolates, begin to release high levels of virus progeny within 4 days. Numerous infected syncytia, comprised of both dendritic and T cells, rapidly develop. Based upon the present study, it appears that conjugates of dendritic cells and T cells, as found in the external linings of organs involved in sexual transmission of HIV-1, represent an important site for the productive phase of HIV-1 infection. Because the affected T cells carry the memory phenotype, this site additionally provides a mechanism for the chronic depletion of CD⁴⁺ memory cells in HIV-1 disease.

Materials and Methods

Culture Medium

Culture medium was prepared as described in Example 1, supra.

Preparation of Cell Suspensions

Skin organ cultures were prepared as described in Example 1, supra. Cells were harvested after collagenase treatment and washed once in culture medium. An average of 57,000±6200 cells were obtained per cm² of skin. Skin cells were studied directly or following sorting on a FACStar$^{PLUS}$ (Becton Dickinson Immunocytometry Systems, Inc. [BDIS], San Jose, Calif.) as described in Example 1, supra. Skin cells were first sorted by size into small single T cells and large cells (free dendritic cells and dendritic cell-T cell conjugates). The large cells were subsequently stained with the fluorescent anti-CD3 and sorted into CD3⁻ (free dendritic cells) and CD3⁺ (dendritic cell-T cell conjugates) cell fractions. Sorted dendritic cells and T cells were 98% pure, as determined by immunofluorescence and peroxidase staining of cytospins (for CD3 and HLA-DR; FIGS. 7B and 7C). A small fraction of free dendritic cells and free T cells in equal numbers were present in the conjugated fraction, probably as a result of dissociation of the conjugates since the CD3⁺ T cells were small HLA-DR⁻ cells (FIG. 7C). For subsequent culture, each viable cell was counted as one, whether free or bound to other cells. Individual conjugates typically contained two cells but could consist of as many as four cells. Therefore, $10^5$ cells of the sorted conjugate fraction represented approximately $4 \times 10^4$ dendritic cells and $6 \times 10^4$ T cells.

Other Cells

Resting T cells were also included in some experiments as the negative control population, not permissive for productive infection. Peripheral blood mononuclear cells (PBMC) were isolated over Ficoll Hypaque gradients (Pharmacia, Upsala, Sweden) and used to provide T cells and adherent monocytes (O'Doherty et al., 1993). The monocytes were dislodged and cultured in Teflon beakers (Savillex Corporation, Minnetonka, Minn.) for up to 14 days. Activated T blasts were prepared by culturing PBMC (approximately $5 \times 10^6$ cells/ml) with 10 μg/ml phytohemagglutinin (PHA, Difco Laboratories, Detroit, Mich.) or 10 ng/ml Staphylococcal enterotoxin E (SEE, Toxin Technology, Madison, Wis.) in 100 mm tissue culture dishes for 2–3 days.

Virus Isolates

The monocytotropic HIV-$1_{Ba-L}$, and the T cell tropic HIV-$1_{IIIB}$ isolates were obtained from The NIH Aids Research and Reference Reagent Program. Patient-derived primary isolates, B 5/85, B 11/88, C 2/86, C 5/84, and D 3/86 (Connor et al., 1993), were kindly donated by Dr. Ruth Connor (Aaron Diamond AIDS Research Center, New York). These had been characterized as syncytia-inducing or non-syncytia inducing using MT-2 cells (Koot et al., 1992). Virus containing supernatants were generated by infecting bulk PBMC cultures that had been stimulated with the superantigen, SEE, while the T cell-tropic isolate also was propagated in the permissive T cell line CEM or in SEE blasts (Cameron et al., 1992). For PCR experiments, viral supernatants were treated with RNase-free DNase I (#776 785 BM) at 50 units per ml for 30 min at 37° C. Heat inactivation was carried out at 60° C. for 30 min.

HIV-1 Infection of Test Cell Suspensions

Five×$10^4$–$1 \times 10^5$ viable cells were added to wells in a 96 well round-bottomed tray (Flow/ICN, Horsham, Pa.). When mixtures of sorted dendritic cells and T cells were studied, $5 \times 10^4$ of each cell type was added per well. Live (100 μl per well, 0.1 MOI), or heat-inactivated virus as control, was added to the cells and incubated for 1.5 hr at 37° C. To wash the cells, the trays were centrifuged for 2–3 min at 2000 rpm at 4° C. (Beckman Centrifuge, GH-3.7 Rotor), the supernatants aspirated, and fresh medium added. Each well was reconstituted to 200 μl with fresh medium and cultured for up to 7 days at 37° C. A dose of 0.1 MOI was chosen to ensure a productive infection within 4–7 days of culture. Lower doses (0.01 MOI) mediated a slower productive infection that was comparable to CEM cells and superantigen-stimulated T blasts.

Detection of infection with HIV-1

Polymerase Chain Reaction (PCR)

Cell lysates were prepared from cells 24–36 hr after exposure, to live virus (Cameron et al., 1992), and aliquots containing $5 \times 10^4$ to $10^5$ cell equivalents were dispensed into 25 μl aliquots and stored at −20° C. ready for amplification by PCR. In any experiment, the number of cells analyzed in each lane was either $5 \times 10^4$ or $10^5$ (the number of cells in the conjugates was evident on the hemocytometer). There was no loss in cell viability during the overnight culture in which entry and reverse transcription of HIV-1 was allowed to take place. To amplify HIV-1 gag sequences the primers SK38 and SK39 (Ou et al., 1988) were used. HLA-DQα sequences were amplified in the same tube as the gag sequences using the primer pairs GH26 and GH27 (Cameron et al., 1992). One primer of each pair was end labeled with γ-($^{32}$P)-ATP (#pb 10168 Amersham, Arlington Heights, Ill.). Approximately 10–20 pmol unlabeled and 5–10 pmol labeled primer ($10^5$ and $10^6$ cpm for HLA-DQα and gag labeled primers, respectively) in a reaction mix containing 3 mM MgCl$_2$ and enzyme buffer were added in 15 μl volumes. Samples were incubated 5 min at 94° C., before adding 10 μl containing 400 μM of each dNTP (#1277 049 BM) and 2 units of Taq polymerase (#M1862 Promega, Madison, Wis.). Amplification was subsequently carried out in a DNA Thermal Cycler (Perkin Elmer Cetus, Norwalk, Conn.): 5 min 94° C., 28 cycles of 94° C. 30 s, 60° C. 30s, and 72° C. 1 min, followed by a 5 min extension at 72° C. at the completion of the run. PCR products (10 μl aliquots) were resolved on an 8% polyacrylamide gel run in 0.5 X TBE. Gels were dried and exposed to XAR-5 film (Kodak, Rochester, N.Y.). Virus copy number was estimated by comparison to the latently infected cell line ACH-2, which contains one copy of provirus in each cell (Folks et al., 1986). A standard curve was set up in each experiment where lanes were labeled: $4=10^4$ ACH-2, $3=10^3$ ACH-2, $2=10^2$ ACH-2, $1=10^1$ ACH-2, $0=1$ ACH-2, and $-=0$ACH-2. $10^5$ normal filler cells were also included in each sample to provide a constant HLA-DQ signal.

RTase Assay

RTase activity in the supernatants of virus pulsed cell cultures was detected using a micro RTase assay on triplicate 10 μl aliquots of culture supernatants (Cameron et al., 1992).

Detection of HIV-1 p24 Antigen

The mouse monoclonal (hybridoma 183; clone H12-5C) (Chesebro et al., 1992) was used to detect HIV-1 p24 antigen at the single cell level by staining cytospins of HIV-1-pulsed cells (see below). p24 levels in culture supernatants were measured at various timepoints using a p24 antigen detection kit (#NEK-060B, New England Nuclear, Boston, Mass.).

Light Microscopy

Preparation of Cytospins

Viable cell counts were determined 4–7 days after exposure of cells to virus and $2 \times 10^4$ cells in 50–100 μl were cytospun onto precleaned microscope slides using a Shandon cytocentrifuge (900 rpm for 5 min, Shandon Inc., Pittsburgh, Pa.). Cytospins were immediately removed from the holders, air dried for 1 hr, and fixed in acetone (Fisher Scientific, Fair Lawn, N.J.) for 10 min at room temperature. Fixed cytospins were dried and rehydrated with Tris buffered saline (TBS, pH 7.6) prior to immunostaining.

Immunostaining

The following primary mouse anti-human monoclonal antibodies were applied to cytospins: anti-CD3 (Leu 4), anti-HLA-DR (9.3C9, ATCC HB180), anti-CD1a (OKT6, ATCC CRL 8020), and control mouse IgG (1 μg/ml, Sigma Chemical Co.). A secondary horseradish peroxidase (HRP) -conjugated F(ab')$_2$ donkey-anti-mouse IgG was added (Jackson ImmunoResearch Laboratories, Inc., West Grove, Pa.) and visualized with the substrate diaminobenzidene (DAB.4HCl, Polysciences Inc., Warrington, Pa.).

Electron Microscopy

Infected skin cell cultures were harvested at least 4 days after exposure to IIIB and the number of viable cells determined. At least $5 \times 10^5$ cells were transferred to an eppendorf tube (Sarstedt, Newton, N.C.) and centrifuged 2–3 min at 2500 rpm (Microspin 12S). The supernatant was aspirated and 100/μl of culture medium containing 5% FCS was added. The cells were gently resuspended with approximately 1 ml of 2.5% glutaraldehyde in 0.1M sodium cacodylate buffer and incubated 1 hr at room temperature. The cells were pelleted, and to minimize cell losses during embedding, resuspended in a small volume of 28% bovine plasma albumin that was overlaid with fixative and allowed to gel. From this point on, the cells were handled like a block of tissue and processed as described (Stössel et al., 1990). Ultrathin sections were contrasted with lead citrate and examined in an EM400 microscope (Philips, Eindhoven, The Netherlands).

Results

Cells Emigrating from Human Skin Explants are Readily Infected with HIV-1

The initial goal of this Example was to evaluate the suscept dendritic cells to HIV-1 infection. The customary approach to isolating skin cells involves trypsin digestion. While such preparations proved permissive for HIV1 infection (data not shown), trypsin-dissociated skin contains an overwhelming majority of keratinocytes (greater than 95%), making direct study of the dendritic cells difficult. Instead, the method described in Example 1, with organ cultures of human skin, whereby dendritic cells selectively emigrate from the explant over 1–3 days. As described above, the dendritic cells are easily identified by their unusual cell shape and motility, and characteristic repertoire of surface antigens. The emigrated populations contained few keratinocytes or macrophages.

However, many small T lymphocytes also were noted in the emigrés, and some were tightly conjugated to dendritic cells, as described in Example 1. As a result, if we labeled the cells that emigrated from skin with anti-MHC class II and anti-CD3 monoclonal antibodies (to identify class II rich-dendritic cells and CD3-rich T cells respectively), three cell populations were apparent: single or free dendritic cells, free T cells, and conjugates of the two cell types (FIG. 7A). As described above, the T cells were TcR$\alpha\beta^+$, with about ⅔ CD4$^+$ and ⅓ CD8$^+$. Most had the phenotype of memory cells, i.e., CD45RO$^+$, CD45RA$^{weak}$, LFA-3$^+$. The dendritic cell-T cell conjugates typically contain one T cell bound to a single dendritic cell (but 2–3 T cells are sometimes seen and were readily counted on a hemocytometer). The conjugates could be sorted from the free dendritic cells and free T cells, with the sorted dendritic cell and T cell fractions 98% pure (FIG. 7B). Some T cells and dendritic cells had disrupted from the sorted conjugates (FIG. 7B bottom panel, arrows). To verify that the conjugates were almost entirely large dendritic cells and small T lymphocytes, the sorted conjugate fractions were spun onto glass slides and stained. The conjugate fractions consisted almost entirely of large CD3$^-$, HLA-DR$^+$ dendritic cells and small CD3$^+$, HLA-DR$^-$ T cells (FIG. 7C).

In spite of the fact that T cells remained tightly coupled to the dendritic cells in culture, there was little evidence for activation such as cell DNA synthesis (FIG. 7D) relative to T cells activated by the lectin, concanavalin A (conA). In addition, sorted dendritic cells and sorted T cells incorporated the same low level of $^3$H-(TdR) as their mixtures in which conjugates reformed (data not shown). This is in contrast to those T cells that bind to dendritic cells carrying antigens or superantigens which proliferate actively (Pancholi et al., 1992; Bhardwaj et al., 1994). When the skin cell suspensions were exposed to live or heat-killed HIV-1, proliferation again was minimal unless a stimulus (ConA) was provided (FIG. 7D).

Figure 8A:
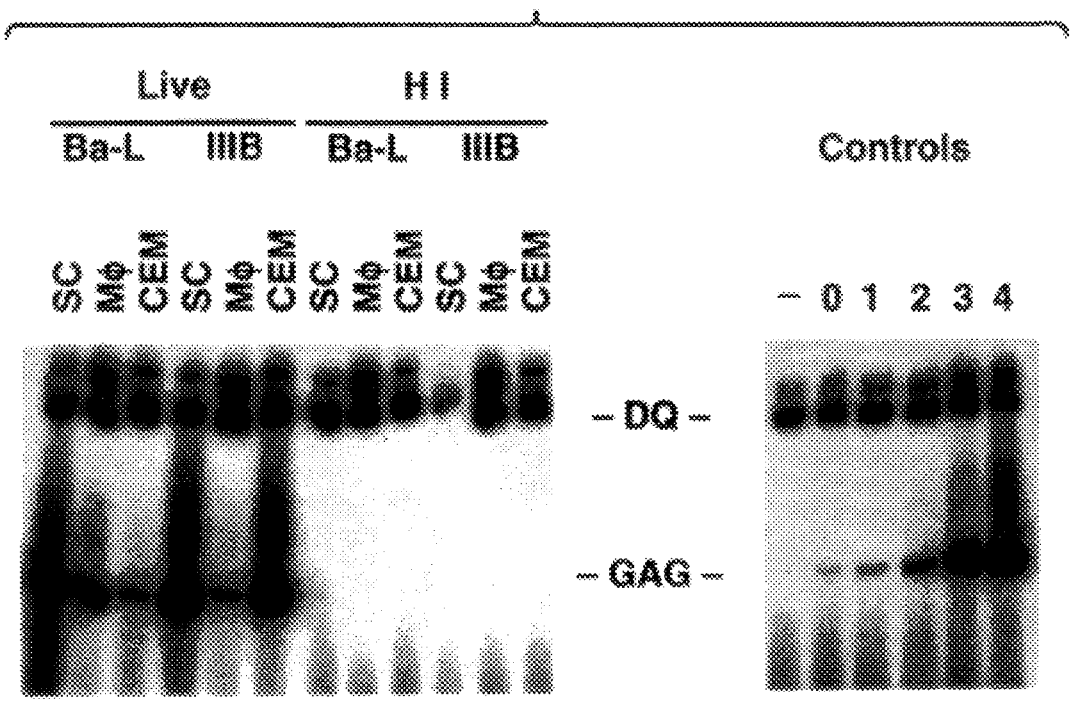
FIG. 8 Skin cell suspensions are readily infected with HIV-1. A. Skin cells (SC), cultured monocytes (Mφ), and CEM cells (CEM) were each pulsed with live or heat-inactivated (HI) HIV-1$_{Ba-L}$ (Ba-L) or HIV-1$_{IIIB}$ (IIIB) for 1.5 hr at 37° C. The cells were washed, cultured for 36 hr, and lysates prepared from equal numbers of cells (50,000 in this experiment). Both HIV-1 gag (GAG) and HLA-DQ (DQ) DNA sequences were amplified by PCR and the products resolved on an 8% polyacrylamide gel. Graded doses of ACH-2 cells (methods) were run as standards (Controls) to estimate the copy numbers of gag signals. B. Skin cells were cultured in the presence of 10% normal human serum (NHS) or fetal calf serum (FCS) to compare susceptibility to infection with two standard HIV-1 isolates. Amplified PCR products were monitored as in part A.
Figure 8B:
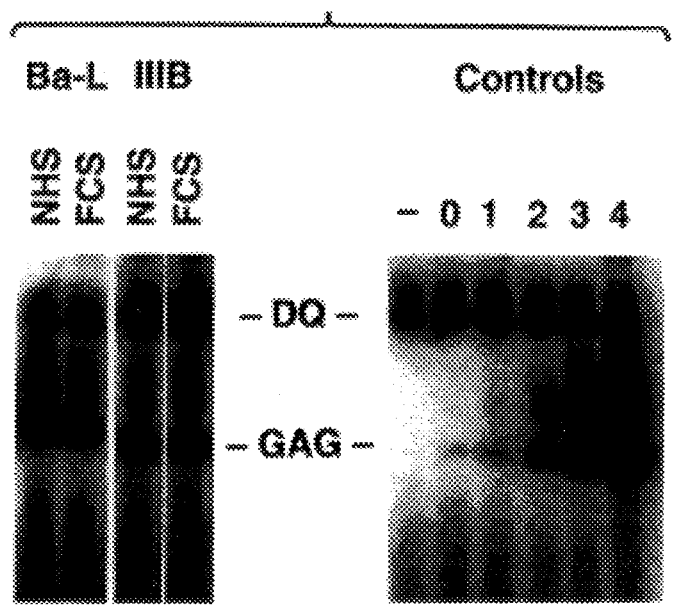

We proceeded to analyze the interaction of HIV-1 with the cutaneous cells, first the bulk mixtures of dendritic cells and T cells, and then time sorted subsets of cells as in FIGS. 7B and 7C. The emigrated mixtures of dendritic cells and T cells were exposed to approximately 0.1 MOI of HIV-1 (FIG. 8). After 1 day, infection was analyzed at the level of viral DNA by PCR amplification of specific gag sequences. Equal numbers of other cell types (monocytes, CEM) were included for comparison, as well as a standard curve utilizing the ACH-2 infected cell line. For both HIV-1$_{Ba-L}$ and HIV-1$_{IIIB}$ isolates, strong infections reproducibly took place. For Ba-L, the signals were equal or greater than that observed with a comparable number of cultured human monocytes, and for IIIB, the signal was equal or greater to the CEM T cell line or PHA-stimulated T blasts (approximately $10^4$ copies per $5\times10^4$ cells; FIG. 8A and below). The skin cells were equally susceptible to infection whether cultured in human or fetal calf serum (FIG. 8B). However, no exogenous mitogen or cytokine was added to the skin cells. In the case of infections with IIIB, the virus was grown initially in the CEM T cell line, so that no exogenous mitogen should be carried over with the HIV inoculum into the skin culture. Therefore, cells derived from normal human skin are permissive for HIV-1 infection, to an extent comparable to standard stimulated populations of monocytes and T cells.

HIV-1 Infection of Skin Cells is Productive: HIV p24 Studies

Figure 9A:
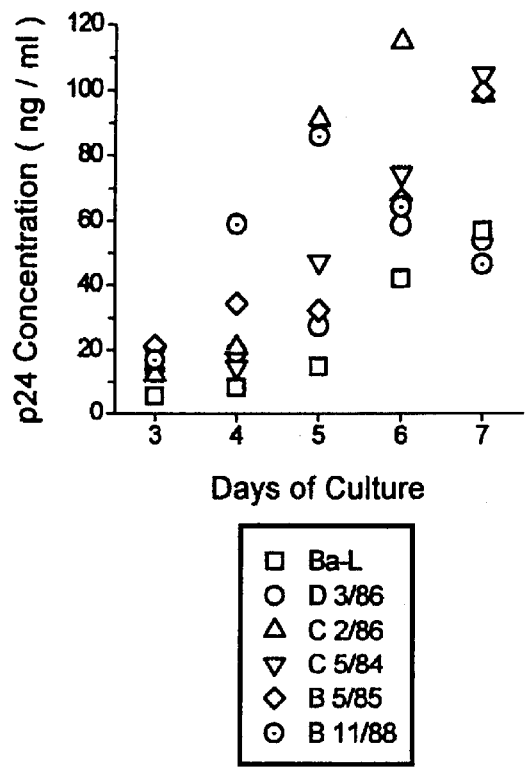
FIG. 9 Cutaneous dendritic cells and T cells together support a productive HIV-1 infection. Skin cells were exposed to several HIV-1 isolates, including HIV-1$_{Ba-L}$ (Ba-L) (□) and the primary isolates: D 3/86 (○), B 5/85 (◇), B 11/88 (⊙), C 5/84 (▽), and C 2/86 (△). Supernatants harvested from days 3–7 of culture were assayed for the presence of p24 antigen (A, means of duplicate samples) and RTase activity (B, means of triplicate samples). Cells exposed to heat-inactivated virus released little of either p24 antigen (0.2–0.9 ng/ml) or RTase (30–100 cpm/µl) into the supernatants.
Figure 9B:
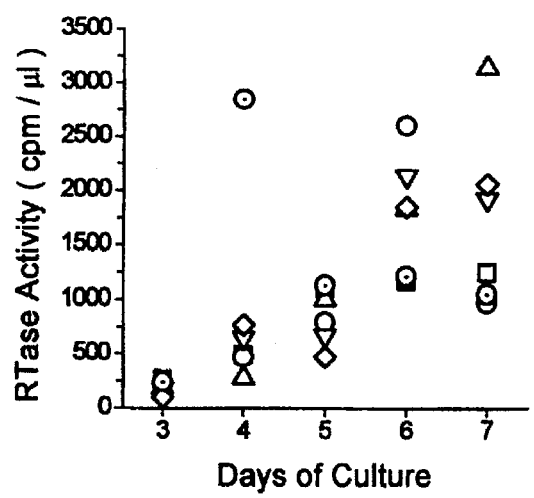

The HIV1 infected skin cells were cultured for periods of 3–7 days, and the culture medium monitored for virion release. High levels of p24 and RTase were released following infection with IIIB (see below), Ba-L and several primary HIV-1 isolates (FIGS. 9A and 9B), provided by Connor et al. (1993). No signals were observed with heat-inactivated preparations of each HIV-1 isolate (not shown).

Figure 10A:
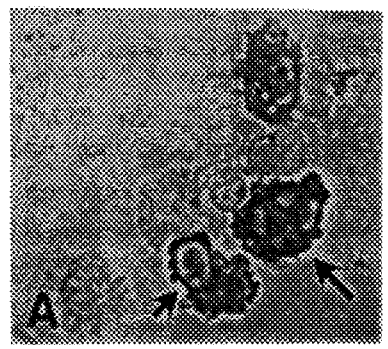
FIG. 10 Dendritic cells and T cells fuse to form syncytia. A–C. Skin cells were pulsed with various HIV-1 isolates: HIV-1$_{Ba-L}$ (A), C 5/84 (B), and B 11/88 (C). After 5 days of culture, cytospins of the cells were stained for expression of HIV-1 p24 antigen using the 183 monoclonal (dark reaction product). Ba-L infected cultures contain enlarged, blast-like, p24$^+$ cells (short arrow, A) and small syncytia (long arrow, B), while all the other HIV-1 isolates generated numerous, large, p24$^+$ syncytia and only infrequent small p24$^+$ cells (not shown). No p24 antigen was expressed by cells exposed to heat-killed HIV. 400X. D–F. Phenotype of syncytia in skin cells infected with HIV-1$_{IIIB}$ and cultured 4 days. Cytospins were stained for CD1a (D), HLA-DR (E), and CD3 (F). Syncytia are arrowed. Magnification is 300X.

To monitor infection at the single cell level, cells were exposed to heat-inactivated or live virus and cultured 4–5 days. Then the cells were cytospun onto glass slides and stained for HIV-1 p24 antigen using a monoclonal from hybridoma 183 (Chesebro et al., 1992). The strong staining provided by the 183 antibody made it possible to identify infected cells directly under a variety of experimental conditions, even though we were obliged to work with relatively small numbers of primary human skin cells. With all 7 isolates tested, and in over 20 such experiments, many p24$^+$ cells were observed, especially syncytia. The number of p24$^+$ syncytia per culture at days 5–7 ranged from 320 to 1800 with the different isolates tested. No p24$^+$ profiles were observed with heat-inactivated HIV. With Ba-L, the p24$^+$ profiles were either blasts, distinctive in appearance relative to the skin dendritic cells and T cells, or small syncytia (FIG. 10A). With IIIB (not shown, but see below) and with all five patient isolates (FIGS. 10B and 10C), numerous large p24$^+$ syncytia were evident by day 4. This was the case whether the initial virus had been characterized as nonsyncytium-inducing (FIG. 10B) or syncytium-inducing (FIG. 10C) in T cell lines. By day 7, many of the cells in cultures that had been exposed to live HIV-1 had died.

HIV-1 Infected Skin Dendritic Cells and T Cells Fuse to Form Syncytia

Figure 10D:
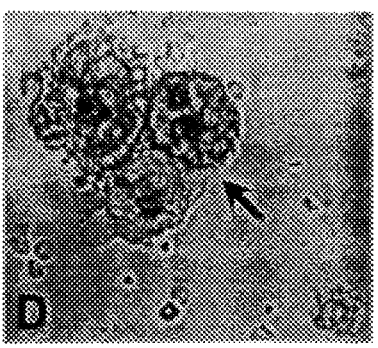
Figure 10B:
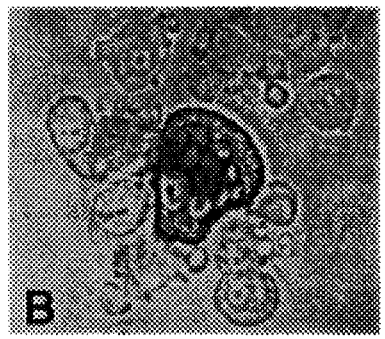
Figure 10E:
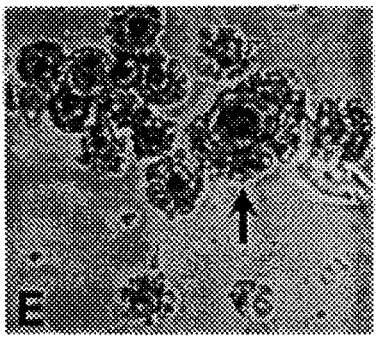
Figure 10C:
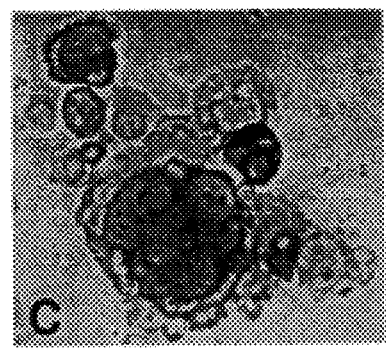
Figure 10F:
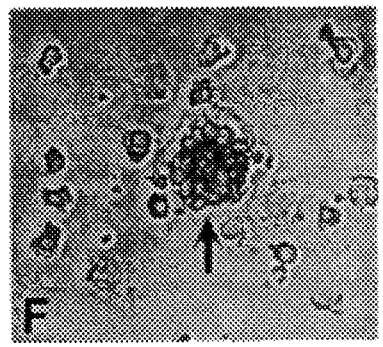

We reasoned that the syncytia developing in skin cells that were exposed to HIV-1 might contain both dendritic cells and T cells. The heterologous nature of the syncytia was evident by antibody staining for dendritic cell (CD1a, strong HLA-DR) and T cell (CD3) markers, phenotyping greater than 100 syncytia per preparation. Some of the syncytia stained moderately with anti-CD1a (FIG. 10D). All stained strongly for MHC class II (FIG. 10E) and CD3 (FIG. 10F).

HIV-1 Infection of Skin Cells is Productive: Electron Microscopy

Electron microscopy was performed on skin cells that had been infected with IIIB and cultured for 4 days. Free dendritic cells were numerous, but rarely contained either budding or fully-formed virions (Table 3). The syncytia had the features of multinucleated dendritic cells, although as mentioned, T cells fused with dendritic cells to form the syncytia (FIGS. 10D–10F). In individual sections, there were 3–8 nuclei that had the same irregular shape and size of single dendritic cells. The cytoplasm contained many electron lucent vesicles, again typical of the acidic vacuoles of dendritic cells (Stössel et al., 1990). Viral budding was evident at foci along the surface of the syncytia (FIG. 11A) and in some intracellular vacuoles (FIG. 11B). Extracellular free virions were seen close to the syncytia surfaces (FIG. 11A).

TABLE 3

Incidence of Viral Budding.

| | # of profiles | Total # of nuclei | Total # viral buds |
|---|---|---|---|
| Syncytia | 10 | 42 | 19 |
| Free DCs | 146 | 146 | 1 |

Figure 12A:
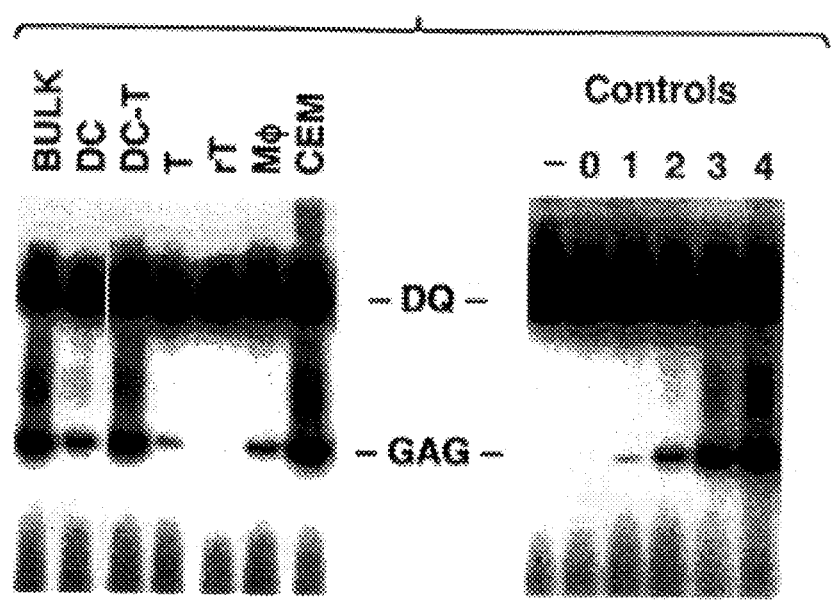
FIG. 12 Dendritic cell-T cell couples, but not separated free dendritic cells or T cells, provide the niche for productive infection with HIV-1. A. Bulk skin cells (BULK), the three individual skin cell fractions (dendritic cells, DC; T cells, T; and dendritic cell-T cell conjugates, DC-T), and control cell populations (resting peripheral blood T cells, rT; cultured monocytes, Mφ; and CEM cells, CEM) were pulsed with HIV-1$_{IIIB}$ (A). Cell lysates were prepared 36 hr later, and equal numbers PCR-amplified for HIV-1 gag (GAG) and HLA-DQ (DQ) products. B,C. As a measure of productive infection of the different subsets of skin cells (Bulk, DC, T, DC-T conjugates, and mixtures of sorted dendritic cells and T cells, DC+T), the presence of HIV p24 antigen (B) and RTase activity (C) was measured in the culture supernatants 4–7 days after pulsing. Cells pulsed with heat-killed HIV-1 produced minimal levels of p24 antigen or RTase activity (as in FIG. 3).

Dendritic Cell-T Cell Conjugates are the Milieu for Productive HIV-1 Infection of Normal Skin Cells: Studies of Cells Isolated by Cell Sorting As described above, the cells that emigrate from skin explants are mixtures of free dendritic cells, free T cells, and conjugates of dendritic cells and T cells. To monitor how each population responded to HIV-1, skin cells were sorted into their respective fractions (FIG. 7). When the sorted populations were infected with IIIB, the dendritic-T cell conjugates gave the strongest infection as measured by PCR analyses for gag-containing transcripts (FIG. 12A). The free dendritic cells gave clear PCR signals (about 100 copies/ 50,000 cells vs. 10,000 copies in the dendritic-T cell conjugates). The low signals observed for dendritic cells pulsed with IIIB were similar to those seen with IIIB-pulsed macrophages. The free T cells had weaker signals than the dendritic cells (10–100 copies). Peripheral blood T cells cultured in parallel (resting T cells) exhibited similar PCR signals (approximately 10 copies) to the sorted skin T cells. These small signals in the "resting" T cell populations may be due to some activation of the T cells by contaminating non-T cells in the E-rosette selected populations.

Figure 12B:
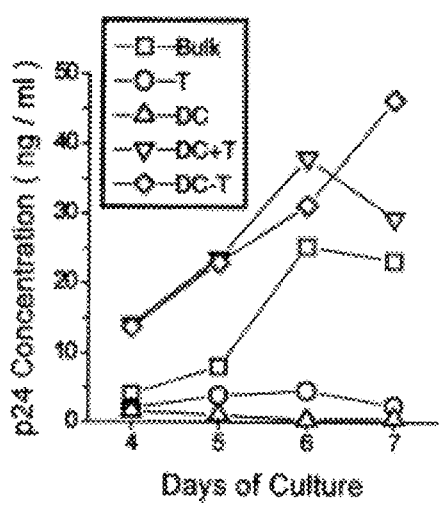
Figure 12C:
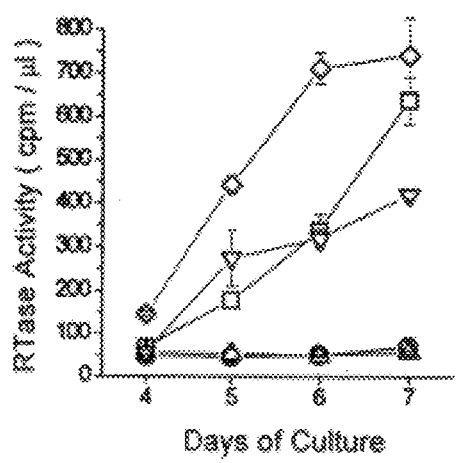
Figure 13A:
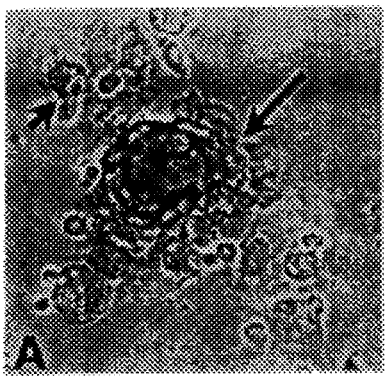
FIG. 13 Dendritic cell-T cell conjugates are the site of syncytium formation. Bulk skin cells, separated skin cell subsets, and mixtures of sorted T cells and dendritic cells were pulsed with live or heat-killed HIV-1$_{IIIB}$ and cultured for 4 days. Cytospins were stained for HIV-1 p24 in bulk skin cells (A), dendritic cells (B), T cells (C), and mixtures of sorted dendritic cells and T cells (D and E) exposed to live HIV-1. Dendritic cell-T cell cocultures pulsed with heat-killed HIV-1 are shown in panel F. Syncytia are identified with long arrows, free dendritic cells with short arrows, and dead syncytia with an *. Magnification is 300X.
Figure 13B:
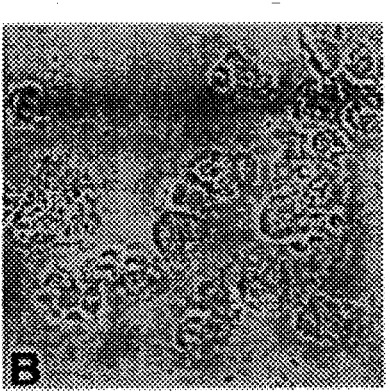
Figure 13C:
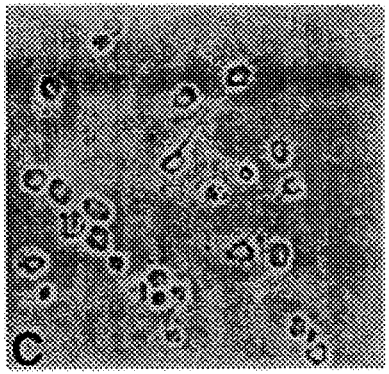
Figure 13D:
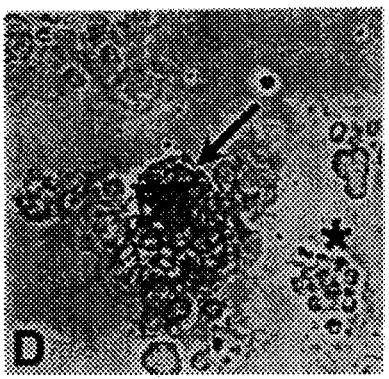
Figure 13E:
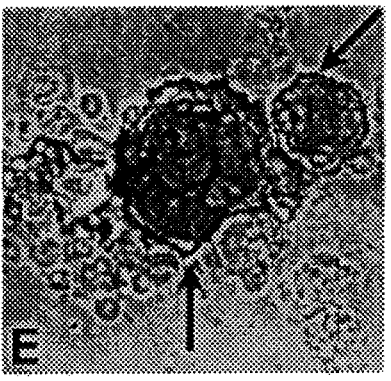
Figure 13F:
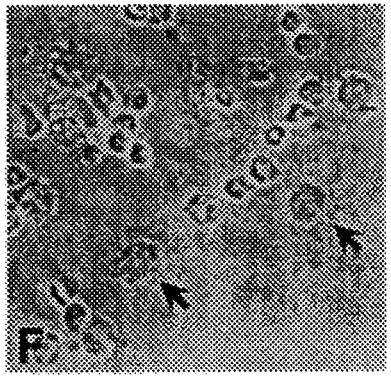

Large differences in the behavior of the sorted skin cell fractions (T cells, dendritic cells, conjugates) were evident when identical numbers of cells in each fraction were infected with HIV-1 and returned to culture. Release of p24 antigen and RTase was not detected from separated dendritic cells or T cells (FIGS. 12B and 12C). However, strong production of p24 and RTase was observed with the dendritic-T cell conjugates, or with recultured mixtures of dendritic cells and T cells in which conjugates formed de novo (FIGS. 12B and 12C). The observations with HIV-p24 staining were striking. In unseparated skin cell suspensions, p24 was confined primarily to large syncytia, as long as live rather than heat-inactivated HIV was applied (FIG. 13A vs. FIG. 13F). When live HIV-1 was applied to isolated dendritic cells or T cells, p24 was not detectable (FIGS. 13B and 13C), except for rare syncytia or infrequent lightly-stained dendritic cells (not shown). When live virus was applied to mixtures of dendritic cells and T cells, or to sorted dendritic-T cell conjugates, many p24+ syncytia developed (FIGS. 13D and 13E). There was no significant loss in viability of cultured, separated dendritic cells and T cells during 4–7 days of culture, but by days 5–7, HIV-infected dendritic cell-T cell conjugates and cocultures began to show a loss of viability as assessed by trypan blue staining. Therefore, productive infection of skin cells by HIV-1 depends upon the presence of dendritic-T cell conjugates.

Discussion

Dendritic Cells as a Site for HIV-1 Infection

These experiments identify a new site for productive infection with HIV-1; i.e., conjugates of dendritic cells and T cells derived from normal skin. Contrasting conclusions have been made on the presence or absence of productive HIV-1 infection within skin dendritic cells in situ (Berger et al., 1992; Kalter et al., 1991). Nonetheless, some proviral DNA almost certainly is found in dendritic cells purified at autopsy from patients who succumb to AIDS (Cimarelli et al., 1994). Our experiments were directed not to infection in patients, but to the susceptibility of normal skin dendritic cells to HIV-1 in vitro. Cutaneous dendritic cells are of interest because analogous cells occur in organs involved in the sexual transmission of HIV-1 (below), and because these cells efficiently activate CD4+ T cells. Skin dendritic cells, purified to be largely free of T cells, can support viral entry as indicated by the presence of gag-containing HIV-1 sequences (FIG. 12). In the two experiments in which we compared infection with monocytotropic (Ba-L, data not shown) and T-tropic (IIIB) isolates, the amount of HIV-1 DNA was several-fold greater following infection with Ba-L. However, cutaneous dendritic cells are not productively infected in our culture, there being little or no release of RTase or p24 antigen, as long as the dendritic cells are separated from the T cells by sorting (FIG. 12).

Instead, it is the conjugates that form between dendritic cells and T cells that give rise to a productive infection with all seven isolates tested. The two cell types even fuse with one another. Dendritic cell-T conjugates are found in afferent lymph (Mackay et al., 1989), suggesting that this cell-cell interaction takes place in situ.

These findings with cutaneous cells differ from prior studies of blood, in which dendritic cells presented foreign antigens or superantigens to responding T cells (Cameron et al., 1992; Cameron et al., 1994). In this prior work, the T cells were proliferating, and the dendritic cells neither became infected nor fused with the T cells. Cultured blood dendritic cells, unlike dendritic cells isolated fresh from blood (O'Doherty et al., 1993), express negligible levels of CD4 and might not be expected to participate in fusion with gp120-expressing cells. In the skin system described here, there is no defined antigenic stimulus, the T cells do not actively synthesize DNA, and yet the dendritic cells and T cells fuse with each other to form numerous infected syncytia. The T cells or the dendritic cells (or both) may be the primary site of HIV-1 infection, express gp120, and then fuse to their counterparts via CD4. It will be necessary to test whether dendritic-T cell conjugates release cytokines that amplify infection in nonconjugated cells.

Although we added no known exogenous stimuli to the skin cultures, it is conceivable that small amounts of some superantigen were carried in the virus-containing supernatants, either in the form of HIV-1 superantigens or from superantigen used to activate the cells in which the HIV-1 was propagated. However, we found no difference in cultures pulsed with the IIIB isolate grown in SEE-activated blasts compared to IIIB grown in the CEM T cell line in the absence of SEE superantigen. The fact that we detected little proliferation even in the presence of large numbers of potent antigen-presenting dendritic cells also argues against typical T cell receptor (TcR)-mediated activation in the skin cultures.

Previous analyses have shown a need for antigen- or mitogen-activation of T cells for active infection with HIV-1 (Siekevitz et al., 1987; Cameron et al., 1992). One now might consider that within cutaneous conjugates (within dendritic cells or T cells, or both together following fusion), there might be some strong stimulus for activating the HIV-1 LTR that is independent of the TcR. Signaling via the CD28/B7 system can activate viral replication in infected T cells (Tong-Starksen et al., 1989; Asjo et al., 1993), and cutaneous dendritic cells express high levels of B7 (Pope et al., 1994; Nestle et al., 1994).

In summary, skin-derived cells are a distinctive and intriguing site for HIV-1 infection because 1) there is a need for dendritic-T cell conjugates, 2) the infection is rapidly productive, giving rise to numerous syncytia and budding virions, 3) the dendritic cells fuse with the T cells, and 4) the T cells may not require signaling via the TcR.

Possible Relevance to Sexual Transmission and Pathogenesis

There is a strong similarity between the skin and the coverings of all organs that are targets for the sexual transmission of HIV-1. The surfaces of the oral cavity, anus, vagina, and uterine cervix are covered with a stratified squamous epithelium that is rich in dendritic cells (reviewed in (Miller et al., 1993)). HIV DNA and RNA have been detected in cervical (Nuovo et al., 1993) and rectal biopsies (Reka and Kotler, 1993) from HIV-infected individuals. SIV-infected cells are found in the cervical and vaginal mucosa of infected rhesus macaques (Miller et al., 1992a; Miller et al., 1992c).

Do conditions exist in situ that correspond to those occurring in cultured skin explants? When mouse skin is transplanted or exposed to contact allergens, the dendritic cells enlarge, express higher levels of MHC class II and begin to migrate (Larsen et al., 1990; Enk et al., 1993). These "activation events" mimic what we observe in explants of human skin, since dendritic cells emigrate and express high levels of MHC class II. Certain insults, e.g., injury and infection, may lead to the same activation of dendritic cells in the linings of the oral, anal, and genital tracts. During the ensuing activation, dendritic cells may engage T cells with the memory phenotype that occur in skin (Foster et at., 1990) and afferent lymph (Mackay et al., 1990). If so, the productive infection that takes place in culture might occur at sites of sexual transmission of HIV.

A loss of T cell memory is the hallmark of HIV-1 infection, and develops early in the clinical course, even prior to a reduction in total $CD4^+$ T cell counts (Murray et al., 1985; Lane et al., 1985). Memory cells carry most of the viral burden in HIV-1 infected individuals (Schnittman et al., 1990). Most memory T cells, that is T cells that have been sensitized by prior exposure to antigen, express the phenotype $CD45RA^-$, $CD45RO^+$, $LFA-3^+$ (Akbar et al., 1988; Sanders et al., 1988). Cells with these markers preferentially home to stimulated vascular endothelium (Picker et al., 1991; Shimizu et al., 1991), and are enriched in afferent lymph (Mackay et al., 1990) suggesting transit through extravascular spaces. In skin, most T cells have the "memory" phenotype (Foster et al., 1990) like the cells that we have studied. Our results provide a mechanism whereby memory cells could become infected in extravascular tissues. If similar events take place in situ there may be no need for an encounter of memory cells with the corresponding cognate antigens, but instead an encounter with activated dendritic cells. These issues can be explored readily in HIV or SIV infected individuals, in particular by using the explant and emigration culture systems described here.

REFERENCES

Akbar, A. N., Terry, L., Timms, A., Beverley, P. C. L., and Janossy, G. Loss of CD45R and gain of UCHL1 reactivity is a feature of primed T cells. J. Immunol. 140, 2171–2178, 1988.

Armstrong, J. A. and Horne, R. Follicular dendritic cells and virus like particles in AIDS related lymphadenopathy. Lancet II., 370–372, 1984.

Asjo, B., Cefai, D., Debre, P., Dudoit, Y., and Autran, B. A Novel Mode of Human Immunodeficiency Virus Type 1 (HIV-1) Activation: Ligation of CD28 Alone Induces HIV-1 Replication in Naturally Infected Lymphocytes. J. Virol. 67, 4395–4398, 1993.

Austyn, J. M., Kupiec-Weglinski, J. W., Hankins, D. F., and Morris, P. J. Migration patterns of dendritic cells in the mouse. Homing to T cell-dependent areas of spleen, and binding within marginal zone. J. Exp. Med. 167: 646–651, 1988.

Barker, C. F., and Billingham, R. E. The role of afferent lymphatics in the rejection of skin homografts. J. Exp. Med. 128: 197–221, 1968.

Berger, R., Gartner, S., Rappersberger, K., Foster, C. A., Wolff, K., and Stingl, G. Isolation of human immunodeficiency virus type 1 from human epidermis: virus replication and transmission studies. J. Invest. Dermatol. 99, 271–277, 1992.

Bhardwaj, N., Hodtsev, A. S., Nisanian, A., Kabak, S., Friedman, S. M., Cole, B. C., and Posnett, D. N. Human T cell responses to Mycoplasma arthritis derived superantigen (MAM). Infect. Immun. 62, 135–144, 1994.

Bhardwaj, N., Young, J. W., Nisanian, A. J., Baggers, J., and Steinman, R. M. Small amounts of superantigen, when presented on dendritic cells, are sufficient to initiate T cell responses. J. Exp. Med. 178, 633–642, 1993.

Biberfeld, P., Chayt, K. J., Marselle, L. M., Biberfeld, G., Gallo, R. C., and Harper, M. E. HTLV-III expression in infected lymph nodes and relevance to pathogenesis of lymphadenopathy. Am. J. Pathol. 125, 436–442, 1986.

Bujdoso, R., Hopkins, J., Dutia, B. M., Young, P., and McConnell, I. Characterization of sheep afferent lymph dendritic cells and their role in antigen carriage. J. Exp. Med. 170: 1285–1302, 1989.

Cameron, P. U., Freudenthal, P. S., Barker, J. M., Gezelter, S., Inaba, K., and Steinman, R. M. ;Dendritic cells exposed to human immunodeficiency virus type-1 transmit a vigorous cytopathic infection to CD4+ T cells. Science 257, 383–387, 1992.

Cameron, P. U., Pope, M., Gezelter, S., and Steinman, R. M. Infection and apoptotic cell death of CD4+ T cells during an immune response to HIV-1 pulsed dendritic cells. Aids Res. Hum. Retroviruses 10, 61–71, 1994.

Chen, L. L., Frank, A. M., Adams, J. C., and Steinman, R. M. Distribution of horseradish peroxidase (HRP)-anti HRP immune complexes in mouse spleen, with special reference to follicular dendritic cells. J. Cell Biol. 79, 184–199, 1978.

Chesebro, B., Wehrly, K., Nishio, J., and Perryman, S. (1992). Macrophage-tropic human immunodeficiency virus isolates from different patients exhibit unusual V3 envelope sequence homogeneity in comparison with T-cell-tropic isolates: definition of critical amino acids involved in cell tropism. J. Virol. 66, 6547–6554.

Cimarelli, A., Zambruno, G., Marconi, A., Girolomoni, G., Bertazzoni, U., and Giannetti, A. Quantitation by competitive PCR of HIV-1 proviral DNA in epidermal Langerhans Cells of HIV-infected patients. J. Acquir. Immune. Defic. Syndr. 7, 230–235, 1994.

Connor, R. I., Mohri, H., Cao, Y., and Ho, D. D. Increased viral burden and cytopathicity correlate temporally with CD4+ T-lymphocyte decline and clinical progression in human immunodeficiency virus type 1-infected individuals. J. Virol. 67, 1772–1777, 1993.

Coombs, R. W., Collier, A. C., Aliain, J.-P., Nikora, B., Leuther, M., Gjerset, G. F., and Corey, L. Plasma viremia in human immunodeficiency virus infection. N. Engl. J. Med. 321, 1626–1631, 1989.

Cooper, K. D., Duraiswamy, N., Kang, S., Crespo, J., and Lee, W. Murine dermal cell suspensions contain T cell activating antigen-presenting cells. J. Invest. Dermatol. 88: 482a, 1987.

Daniels, T. E. Human mucosal Langerhans cells: Postmortem identification of regional variations in oral mucosa. J. Invest. Dermatol. 82, 21–24, 1984.

Embretson, J., Zupancic, M., Ribas, J. L., Burke, A., Racz, P., Tenner-Racz, K., and Haase, A. T. Massive covert infection of helper T lymphocytes and macrophages by HIV during the incubation period of AIDS. Nature 362, 359–362, 1993.

Enk, A. H., Angeloni, V. L., and Udey, S. I. An essential role for Langerhans cell-derived IL-1 beta in the initiation of primary immune responses in skin. J. Immunol. 150, 3698–3704, 1993.

Flechner, E. R., Freudenthal, P. S., Kaplan, G., and Steinman R. M. Antigen-specific T lymphocytes efficiently cluster with dendritic cells in the human primary mixed-leukocyte reaction. Cell Immunol. 111: 183–195, 1988.

Folks, T., Powell, D. M., Lightfoote, M. M., Benn, S., Martin, M. A., and Fauci, A. S. Induction of HTLV-III/LAV from a nonvirus-producing T-cell line: implications for latency. Science 231, 600–602, 1986.

Foster, C. A., Yokozeki, H., Rappersberger, K., Koning, F., Volc-Platzer, B., Reiger, A., Coligan, J. E., Wolff, K., and Stingl, G. Human epidermal T cells predominantly belong to the lineage expressing alpha/beta T cell receptor. J. Exp. Med. 171, 997–1013, 1990.

Frey, J. R. and Wenk, P. Experimental studies on the pathogenesis of contact eczema in the guinea pig. Intl Arch. Allergy Appl. Immunol. 11: 81–100, 1957.

Gray, D. Immunological memory. Ann. Rev. Immunol. 11, 49–77, 1993.

Hanna, Jr., M. G. and Szakal, A. K. Localization of 125I-labeled antigen in germinal centers of mouse spleen: histologic and ultrastructural autoradiographic studies of the secondary immune reaction. J. Immunol. 101, 949–962, 1968.

Heufler, C., Koch, F., and Schuler G. Granulocyte-macrophage colony-stimulating factor and interleukin-1 mediate the maturation of murine epidermal Langerhans cells into potent immunostimulatory dendritic cells. J. Exp. Med 167: 700–705, 1987.

Ho, D. D., Moudgil, T., and Alam, M. Quantitation of human immunodeficiency virus type 1 in the blood of infected persons. N. Engl. J. Med. 321, 1621–1625, 1989.

Humphrey, J. H., Grennan, D., and Sundaram, V. The origin of follicular dendritic cells in the mouse and the mechanism of trapping of immune complexes on them. Eur. J. Immunol. 14, 859–868, 1984.

Inaba, K. and Steinman, R. M. Resting and sensitized T lymphocytes exhibit distinct stimulatory (antigen-presenting cell) requirements for growth and lymphokine release. J. Exp. Med. 160, 1717–1735, 1984.

Inaba, K. and Steinman, R. M. Accessory cell-T lymphocyte interactions: antigen dependent and independent clustering. J. Exp. Med. 163, 247–261, 1986.

Inaba, K., Metlay, J. P., Crowley, M. T., and Steinman, R. M. Dendritic cells pulsed with protein antigens in vitro can prime antigen-specific, MHC-restricted T cells in situ. J. Exp. Med. 172: 631–640, 1990.

Inaba, K., Witruer-Pack, M., Inaba, M., Hathcock, K. S., Sakuta, H., Azuma, M., Yagita, H., Okumura, K., Linsley, P. S., Ikehara, S., Muramatsu, S., Hodes, R. J., and Steinman, R. M. The tissue distribution of the B7-2 costimulator in mice: abundant expression on dendritic cells in situ and during maturation in vitro. J. Exp. Med. In Press: 1994.

Kalter, D. C., Greenhouse, J. J., Orenstein, J. M., Schnittman, S. M., Gendelman, H. E., and Meltzer, M. S. Epidermal Langerhans cells are not principal reservoirs of virus in HIV disease. J. Immunol. 146, 3396–3404, 1991.

Kaplan, G., Nusrat, A., Witmer, M. D., Nath, I., and Cohn, Z. A. Distribution and turnover of Langerhans cells during delayed immune responses in human skin. J. Exp. Med. 165, 763–776, 1987.

Klatzmann, D., Barre'-Sinoussi, F., Nugeyre, M. T., Dauguet, C., Griscelli, C., Brun-Vezinet, F., Rouzioux, C., Gluckman, J. C., Chermann, J. C., and Montagnier, L. Selective tropism of lymphadenopathy associated virus (LAV) for helper-inducer T lymphocytes. Science 225, 59–63, 1984.

Knight, S. C., Balfour, B. M., O'Brien J., Buttifant, L., Sumerska, T., and Clark, J. Role of veiled cells in lymphocyte activation. Eur. J. Immunol. 12: 1057–1060, 1982.

Knight, S. C., Farrant, J., Bryant, A., Edwards, A. J., Burman, S., Lever, A., Clarke, J., and Webster A. D. B. Non-adherent, low-density cells from human peripheral blood contain dendritic cells and monocytes, both with veiled morphology. Immunol. 57: 595–603, 1986.

Koot, M., Vos, ; A. H. V., Keet, R. P. M., De Goede, R. E. Y., Dercksen, M. W., Terpstra, F. G., Coutinho, R. A., Miedema, F., and Tersmette, M. HIV-1 biological phenotype in long-term infected individuals evaluated with an MT-2 cocultivation assay. AIDS 6, 49–54, 1992.

Kripke, M. L., Munn, C. G., Jeevan, A., Tang, J.-M., and Bucana, C. Evidence that cutaneous antigen-presenting cells migrate to regional lymph nodes during contact sensitization. J. Immunol. 145: 2833–2838, 1990.

Lane, H. C., Depper, J. M., Greene, W. C., Whalen, G., Waldmann, T. A., and Fauci, A. S. Qualitative analysis of immune function in patients with the acquired immunodeficiency syndrome. New Engl. J. Med. 313, 79–84, 1985.

Larsen, C. P., Ritchie, S. C., Pearson, T. C., Linsley, P. S., and Lowry, R. P. Functional expression of the costimulatory molecule, B7/BB1, on murine dendritic cell populations. J. Exp. Med. 176: 1215–1220, 1992.

Larsen, C. P., Steinman, R. M., Witruer-Pack, M. D., Hankins, D. F., Morris, P. J., and Austyn, J. M. Migration and maturation of Langerhans cells in skin transplants and explants. J. Exp. Med. 172, 1483–1493, 1990.

Lens, J. W., Drexhage, H. A., Benson, W., and Balfour, B. M. A study of cells present in lymph dmining from a contact allergic reaction in pigs sensitized to DNFB. Immunol. 49: 415–422, 1983.

Lenz, A., Heine, M., Schuler, G., and Romani, N. Human and murine dermis contain dendritic cells: Isolation by means of a novel method and phenotypical and functional characterization. J. Clin. Invest. 92: 2587–2596, 1993.

Liu, L. M., and MacPherson, G. G. Antigen acquisition by dendritic cells: Intestinal dendritic cells acquire antigen administered orally and can prime naive T cells "in vivo". J. Exp. Med. 177: 1299–1307, 1993.

Macatonia, S. E., Knight S. C., Edwards, A. J., Griffiths, S., and Fryer, P. Localization of antigen on lymph node dendritic cells after exposure to the contact sensitizer fluorescein isothiocyanate. J. Exp. Med. 166: 1654–1667, 1987.

Mackay, C. R., Hein, W. R., Brown, M. H., and Matzinger, P. Unusual expression of CD2 in sheep: implications for T cell interactions. Eur. J. Immunol. 18, 1681–1688, 1989.

Mackay, C. R., Marston, W. L., and Dudler, L. Naive and memory T cells show distinct pathways of lymphocyte recirculation. J. Exp. Med. 171, 801–818, 1990.

Miller, C. J., Alexander, N. J., Vogel, P., Anderson, J., and Marx, P. A. Mechanism of genital transmission of SIV: a hypothesis based on transmission studies and the location of SIV in the genital tract of chronically infected female rhesus macaques. J. Med. Primatol. 21, 64–68, 1992a.

Miller, C. J., McChesney, M., and Moore, P. F. Langerhans cells, macrophages and lymphocyte subsets in the cervix and vagina of rhesus macaques. Lab. Invest. 67, 628–634, 1992b.

Miller, C. J., Vogel, P., Alexander, N. J., Sutjipto, S., Hendrickx, A. G., and Marx, P. A. Localization of SIV in the genital tract of chronically infected female rhesus macaques. Am. J. Pathol. 141, 655–660, 1992c.

Miller, C. J., McGhee, J. R., and Gardner, M. B. Biology of Disease. Mucosal Immunity, HIV transmission, and AIDS. Lab. Invest. 68, 129–145, 1993.

Murray, H. W., Hillman, J. K., Rubin, B. Y., Kelly, C. D., Jacobs, J. L., Tyler, L. W., Donelly, D. M., Carriero, S. M., Godbold, J. H., and Roberts, R. B. Patients at risk for AIDS-related opportunistic infections. Clinical manifestations and impaired gamma interferon production. New Engl. J. Med. 313, 1504–1510, 1985.

Nestle, F. O., Thompson, C., Shimizu, .Y., Turka, L. A., and Nickoloff, B. J. Costimulation of superantigen-activated T lymphocytes by autologous dendritic cells is dependent on B7. Cell. Immunol. 156, 220–229, 1994.

Nossal, G. J. V., Abbot, A., Mitchell, J., and Lummus, Z. Antigen in immunity. XV. Ultrastructural features of antigen capture in primary and secondary lymphoid follicles. J. Exp. Med. 127, 277–296, 1968.

Nuovo, G. J., Forde, A., MacConnell, P., and Fahrenwald, R. In situ detection of PCR-amplified HIV-1 nucleic acids and tumour necrosis factor cDNA in cervical tissues. Am. J. Pathol. 143, 40–48, 1993.

O'Doherty, U., Steinman, R. M., Peng, M., Cameron, P. U., Gezelter, S., Kopeloff, I., Swiggard, W. J., Pope, M., and Bhardwaj, N. Dendritic cells freshly isolated from human blood express CD4 and mature into typical immunostimulatory dendritic cells after culture in monocyte-conditioned medium. J. Exp. Med. 178, 1067–1078, 1993.

Ou, C.-Y., Kwok, S., Mitchell, S. W., Mack, D. H., Shinsky, J. J., Krebs, J. W., Feorino, P., Warfield, D., and Schochetman, G. DNA amplification for direct detection of HIV-1 in DNA of peripheral blood mononuclear cells. Science 239, 295–297, 1988.

Pancholi, P., Steinman, R. M., and Bhardwaj, N. Dendritic cells efficiently immunoselect mycobacterial-reactive T cells in human blood, including clonable antigen-reactive precursors. Immunol. 76, 217–224, 1992.

Pancholi, P., Steinman, R. M., and Bhardwaj, N. An approach to isolating T cell lines that react to antigens presented on the surface of dendritic cells. Clin. Exp. Immunol. 85: 349–356, 1991.

Pantaleo, G., Graziosi, C., Demarest, J. F., Butini, L., Montroni, M., Fox, C. H., Orenstein, J. M., Kotler, D. P., and Fauci, A. S. HIV infection is active and progressive in lymphoid tissue during the clinically latent stage of disease. Nature 362, 355–358, 1993.

Piatak Jr., M., Saag, M. S., Yang, L. C., Clark, S. J., Kappes, J. C., Luk, K.-C., Hahn, B. H., Shaw, G. M., aM Lifson, J. D. High levels of HIV-1 in plasma during all stages of infection determined by competitive PCR. Science 259, 1749–1754, 1993.

Picker, L. J., Kishimoto, T. K., Smith, C. W., Warhock, R. A., and Butcher, E. C. ELAM-1 is an adhesion molecule for skin-homing T cells. Nature 349, 796–799, 1991.

Pugh, C. W., MacPherson, G. G., and Steer, H. W. Characterization of nonlymphoid cells derived from rat peripheral lymph. J. Exp. Med. 157: 1758–1779, 1983.

Racz, P., Tenner-Racz, K., Kahl, C., Feller, A. C., Kern, P., and Dietrich, M. Spectrum of morphologic changes of lymph nodes from patients with AIDS or AIDS-related complexes. Prog. Allergy 37, 81–181, 1986.

Reka, S. and Kotler, D. P. Detection and localization of HIV RNA and TNF mRNA in rectal biopsies from patients with AIDS. Cytokine 5, 305–308, 1993.

Rhodes, J. M., Balfour, B. M., Blom, J., and Agger, R. Comparison of antigen uptake by peritoneal macrophages and veiled cells from the thoracic duct using isotope-, FITC, or gold-labelled antigen. Immunol. 68: 403–409, 1989.

Richters, C. D., Hoefsmit, E. C. M., van Baaren, J., Hoekstra, M. J., du Pont, J. S., and Kamperdyk, E. W. A. Migratory properties of human skin dendritic cells. J. Invest. Dermatol. Submitted, 1994.

Romani, N., Lenz, A., Glassel, H., Stössel, H., Stanzl, U., Majdic, O., Fritsch, P., and Schuler, G. Cultured human Langerhans cells resemble lymphoid dendritic cells in phenotype and function. J. Invest Dermatol. 93: 600–609, 1989.

Saksela, K., Stevens, C., Rubinstein, P., and Baltimore, D. Human immunodeficiency virus type 1 mRNA expression in peripheral blood cells predicts disease progression independently of the numbers of CD4+ lymphocytes. Proc. Natl. Acad. Sci. USA 91, 1104–1108, 1994.

Sanders, M. E., Makgoba, M. W., Sharrow, S. O., Stephany, D., Springer, T. A., Young, H. A., and Shaw, S. Human memory T lymphocytes express increased levels of three cell adhesion molecules (LFA-3, CD2, and LFA-1) and three other molecules (UCHLI, CDw29, and Pgp-1) and have enhanced IFN-gamma production. J. Immunol. 140, 1401–1407, 1988.

Schnittman, S. M., Lane, H. C., Greenhouse, J., Justement, J. S., Baseler, M., and Fauci, A. S. Preferential infection of CD4+ memory T cells by human immunodeficiency virus type 1: evidence for a role in the selective T-cell functional defects observed in infected individuals. Proc. Natl. Acad. Sci. USA 87, 6058–6062, 1990.

Schuler, G., and Steinman, R. M. Murine epidermal Langerhans cells mature into potent immunostimulatory dendritic cells in vitro. J. Exp. Med. 161: 526–546, 1985.

Shimizu, Y., Shaw, S., Graber, N., Gopal, T. V., Horgan, K. J., Van Secenter, G. A., and Newman, W. Activation-independent binding of human memory T cells to adhesion molecule ELAM-1. Nature 349, 799–802, 1991.

Siekevitz, M., Josephs, S. F., Dukovich, M., Peffer, N., Wong-Staal, F., and Greene, W. C. Activation of the HIV-1 LTR by T cell milogens and the trans-activator protein of HTLV-1. Science 238, 1575–1578, 1987.

Silberberg-Sinakin, I., Thorbecke, G. J., Baer, R. L., Rosenthal, S. A., and Berezowsky V. Antigen-bearing Langerhans cells in skin, dermal lymphatics and in lymph nodes. Cell. Immunol. 25: 137–151, 1976.

Smith, S. H., Brown, M. H., Rowe, D., Callard, R. E., and Beverley, P. C. L. Functional subsets of human helper-inducer cells defined by a new monoclonal antibody, UCHL1. Immunol 58: 63–70, 1986.

Sontheimer, R. D. The mixed epidermal cell-lymphocyte reaction. II. Epidermal Langerhans cells are responsible for the enhanced allogeneic lymphocyte-stimulating capacity of normal human epidermal cell suspensions. J. havest. Dermatol. 85: 21s–26s, 1985.

Sornasse, T., Flareand, V., DeBecker, G., Bazin, H., Tielemans, F., Thielemans, K., Urbain, J., Leo, O., and Moser, M. Antigen-pulsed dendritic cells can efficiently induce an antibody response in vivo. J. Exp. Med. 175: 15–21, 1992.

Spiegel, H., Herbst, H., Niedobitek, G., Foss, H.-D., and Stein, H. Rapid communication. Follicular dendritic cells are a major reservoir for human immunodeficiency virus type 1 in lymphoid tissues facilitating infection of CD4+ T-helper cells. Am. J. Pathol. 140, 15–22, 1992.

Steinman, R. M. The dendritic cell system and its role in immunogenicity. Ann. Rev. Immunol. 9, 271–296, 1991.

Stössel, H., Koch, F., Kämpgen, E., Stöger, P., Lenz, A., Heufler, C., Romani, N., and Schuler, G. Disappearance of certain acidic organelles (endosomes and Langerhans cell granules) accompanies loss of antigen processing capacity upon culture of epidermal Langerhans cells. J. Exp. Med. 172, 1471–1482, 1990.

Symington, F. W., Brady, W., and Linsley, P. S. Expression and function of B7 on human epidermal Langerhans cells. J. Immunol. 150: 1286–1295, 1993.

Szakal, A. K., Kosco, M. H., and Tew, J. G. Microanatomy of lymphoid tissue during humoral immune responses: structure function relationships. Ann. Rev. Immunol. 7, 91–109, 1989.

Teunissen, M. B. M, Wormmeester, J., Krieg, S. R., Peters, P. J., Vogels, L M. C., Kapsenberg, M. L., and Bos, J. D. Human epidermal Langerhans cells undergo profound morphologic and phenotypical changes during in vitro culture. J. Invest. Dermatol. 94: 166–173, 1990.

Tong-Starksen, S. E., Luciw, P. A., and Peterlin, M. Signaling through T lymphocyte surface proteins, TCR/CD3 and CD28, activates the HIV-1 long terminal repeat. J. Immunol. 142, 702–707, 1989.

Tse, Y., Cooper, K. D. Cutaneous dermal Ia+ cells are capable of initiating delayed type hypersensitivity responses. J. Invest. Dermatol. 94: 267–272, 1990.

van Noesel, C. J. M., Gruters, R. A., Terpstra, F. G., Schellekens, P. Th. A., van Lier, R. A. W., and Miedema, F. Functional and Phenotypic evidence for a selective loss of memory T cells in asymptomatic Human Immunodeficiency Virus-Infected Men. J. Clin. Invest. 86, 293–299, 1994.

Witruer-Pack, M. D., Olivier, W., Valinsky, J., Schuler, G., and Steinman, R. M. Granulocyte/macrophage colony-stimulating factor is essential for the viability and function of cultured murine epidermal Langerhans cells. J. Exp. Med. 166: 1484–1498, 1987.

Wood, G. S., and Freudenthal, P. S. CD5 monoclonal antibodies react with human peripheral blood dendritic cells. Am. J. Pathol. 141: 789–795, 1992.

Wood, G. S., Warner, N. L., and Warnke, R. A. Anti-Leu-3/T4 antibodies react with cells of monocyte/macrophage and Langerhans lineage. J. Immunol. 131, 212–216, 1983.

Zack, J. A., Arrigo, S. J., Weitsman, S. R., Go, A. S., Haislip, A., and Chen, I. S. Y. HIV-1 entry into quiescent primary lymphocytes: Molecular analysis reveals a labile, latent viral structure. Cell 61, 213–222, 1990.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

Various references are cited throughout this specification, each of which is incorporated herein by reference in its entirety.

What is claimed is:

1. An in vitro method for the identification of agents capable of inhibiting human immunodeficiency virus (HIV) infection of dendritic cell-T lymphocyte conjugates found in skin and mucous membranes related to skin, comprising the following steps:

a) contacting a first skin explant with an agent to be assayed for its ability to inhibit HIV infection of dendritic cell-T lymphocyte conjugates;

b) floating the first skin explant dermal side down in culture medium at 37° C.;

c) allowing dendritic cells and T-lymphocytes to emigrate from the skin explant of (b) and form dendritic cell-T lymphocyte conjugates;

d) floating a second control skin explant dermal side down in control culture medium, which is not contacted with the agent of step (a), at 37° C.;

e) allowing dendritic cells and T-lymphocytes to emigrate from the skin explant of step (d) and form dendritic cell-T lymphocyte conjugates;

f) exposing said conjugates of both the first and second skin explants to infectious HIV; and, g) determining whether said conjugates become productively infected with HIV;

wherein a decrease in the level of HIV infection in conjugates from the first skin explant, as compared to conjugates in the second skin explant, is indicative of said agent being capable of inhibiting HIV infection of dendritic cells and T-lymphocytes obtained from skin and mucous membranes related to skin.

2. The method according to claim 1, wherein the level of HIV infection is determined by a method selected from the group consisting of analyzing viral mRNA expression, detecting the amount of virus released, detecting HIV antigens through HIV-specific immunoassays, detecting the formation of dendritic cell-T lymphocyte syncytia, and detecting the presence of budding or mature HIV virions.

3. The method according to claim 1, wherein the level of HIV infection is determined by PCR amplification of proviral HIV gag sequences.

4. The method according to claim 2, wherein the amount of virus released is ascertained through the detection of p24 antigen levels in culture supernatants or the detection of reverse transcriptase activity in culture supernatants.

5. The method according to claim 2, wherein the formation of dendritic cell-T lymphocyte syncytia is determined by immunostaining for the presence of dendritic cell and T lymphocyte markers.

6. The method according to claim 5, wherein the dendritic cell marker is selected from the group consisting of MHC Class II antigens and CD1a, and the T lymphocyte marker is selected from the group consisting of CD2, CD3, CD45RO, and LFA-3.

7. The method according to claim 1, wherein the agent is applied directly to the skin prior to floating the explant in culture medium.

8. The method according to claim 1, wherein the agent is present in the culture medium.

9. The method according to claim 1, wherein the mucous membrane is selected from the group consisting of anal, vaginal, penile, cervical, and oral epithelium.

10. The method according to claim 1, wherein the skin is obtained from a human subject.

11. The method according to claim 1, wherein the infectious HIV consists of cell-free virus.

12. The method according to claim 1, wherein the infectious HIV consists of HIV-infected cells.

* * * * *

UNITED STATES PATENT AND TRADEMARK OFFICE
CERTIFICATE OF CORRECTION

PATENT NO. : 5,627,025
DATED : May 6, 1997
INVENTOR(S) : Ralph M. Steinman; Melissa Pope; Michiel Betjes; and Lloyd Hoffman It is certified that error appears in the above-indentified patent and that said Letters Patent is hereby corrected as shown below:

On the cover page of the patent, please add the following Assignee

--Cornell Research Foundation, Inc., Ithaca, New York--.

Signed and Sealed this

Seventeenth Day of February, 1998

Attest:

BRUCE LEHMAN

*Attesting Officer*    *Commissioner of Patents and Trademarks*